US010433710B1

(12) United States Patent
Griffin

(10) Patent No.: US 10,433,710 B1
(45) Date of Patent: Oct. 8, 2019

(54) IN-VIVO IMAGING AND ACCESS SYSTEM UTILIZING A CANTED WORKING CHANNEL AND A RING ILLUMINATED SURGICAL CAMERA

(71) Applicant: InnovaQuartz LLC, Phoenix, AZ (US)

(72) Inventor: Stephen E. Griffin, Peoria, AZ (US)

(73) Assignee: InnovaQuartz Inc., Phoenix, AZ (US)

( * ) Notice: Subject to any disclaimer, the term of this patent is extended or adjusted under 35 U.S.C. 154(b) by 0 days.

(21) Appl. No.: 15/986,468

(22) Filed: May 22, 2018

(51) Int. Cl.
| *A61B 1/05* | (2006.01) |
| *A61B 1/06* | (2006.01) |
| *A61B 1/00* | (2006.01) |
| *A61B 1/07* | (2006.01) |
| *A61B 1/307* | (2006.01) |

(52) U.S. Cl.
CPC ............ *A61B 1/00096* (2013.01); *A61B 1/07* (2013.01); *A61B 1/05* (2013.01); *A61B 1/0638* (2013.01); *A61B 1/0676* (2013.01); *A61B 1/0684* (2013.01); *A61B 1/307* (2013.01)

(58) Field of Classification Search
CPC . A61B 1/00096; A61B 1/00098; A61B 1/012; A61B 1/018; A61B 1/05; A61B 1/0638; A61B 1/0676; A61B 1/0684
See application file for complete search history.

(56) References Cited

U.S. PATENT DOCUMENTS

| 6,404,984 B1* | 6/2002 | Parvulescu | A61B 1/041 348/66 |
| 6,449,006 B1* | 9/2002 | Shipp | H04N 7/183 348/70 |
| 6,551,240 B2 | 4/2003 | Henzler | |
| 6,659,940 B2 | 12/2003 | Adler | |
| 7,668,450 B2 | 2/2010 | Todd et al. | |
| 8,202,214 B2 | 6/2012 | Doguchi et al. | |
| 8,308,637 B2 | 11/2012 | Ishigami et al. | |
| 8,512,232 B2 | 8/2013 | Rothberg et al. | |
| 8,801,255 B2 | 8/2014 | Kudo | |
| 9,826,892 B2 | 11/2017 | Dresher et al. | |
| 9,838,576 B2 | 12/2017 | Haraguchi et al. | |
| 2003/0050534 A1* | 3/2003 | Kazakevich | A61B 1/0607 600/178 |
| 2005/0117027 A1* | 6/2005 | Fukuhara | B60R 11/04 348/222.1 |
| 2005/0234296 A1* | 10/2005 | Saadat | A61B 1/0008 600/129 |
| 2007/0038030 A1 | 2/2007 | Kaneko et al. | |
| 2007/0039077 A1 | 2/2007 | Takami | |
| 2008/0283770 A1* | 11/2008 | Takahashi | A61B 1/043 250/458.1 |
| 2009/0306474 A1* | 12/2009 | Wilson | A61B 1/041 600/109 |
| 2016/0058383 A1* | 3/2016 | Hellstrom | A61B 5/6852 600/430 |
| 2017/0353656 A1* | 12/2017 | Ramones | H04N 5/23238 |

* cited by examiner

*Primary Examiner* — Aaron B Fairchild

(57) ABSTRACT

Diagnostic and surgical devices that include endoscopic working channels that are non-parallel to the longitudinal axis of an endoscopic tip. Preferably, the devices include a ring illuminated surgical camera (RISC) carried in the endoscopic tip, e.g., perpendicular to the face of the endoscopic tip, and include the endoscopic working channels terminating at openings in the face of the endoscopic tip.

15 Claims, 14 Drawing Sheets

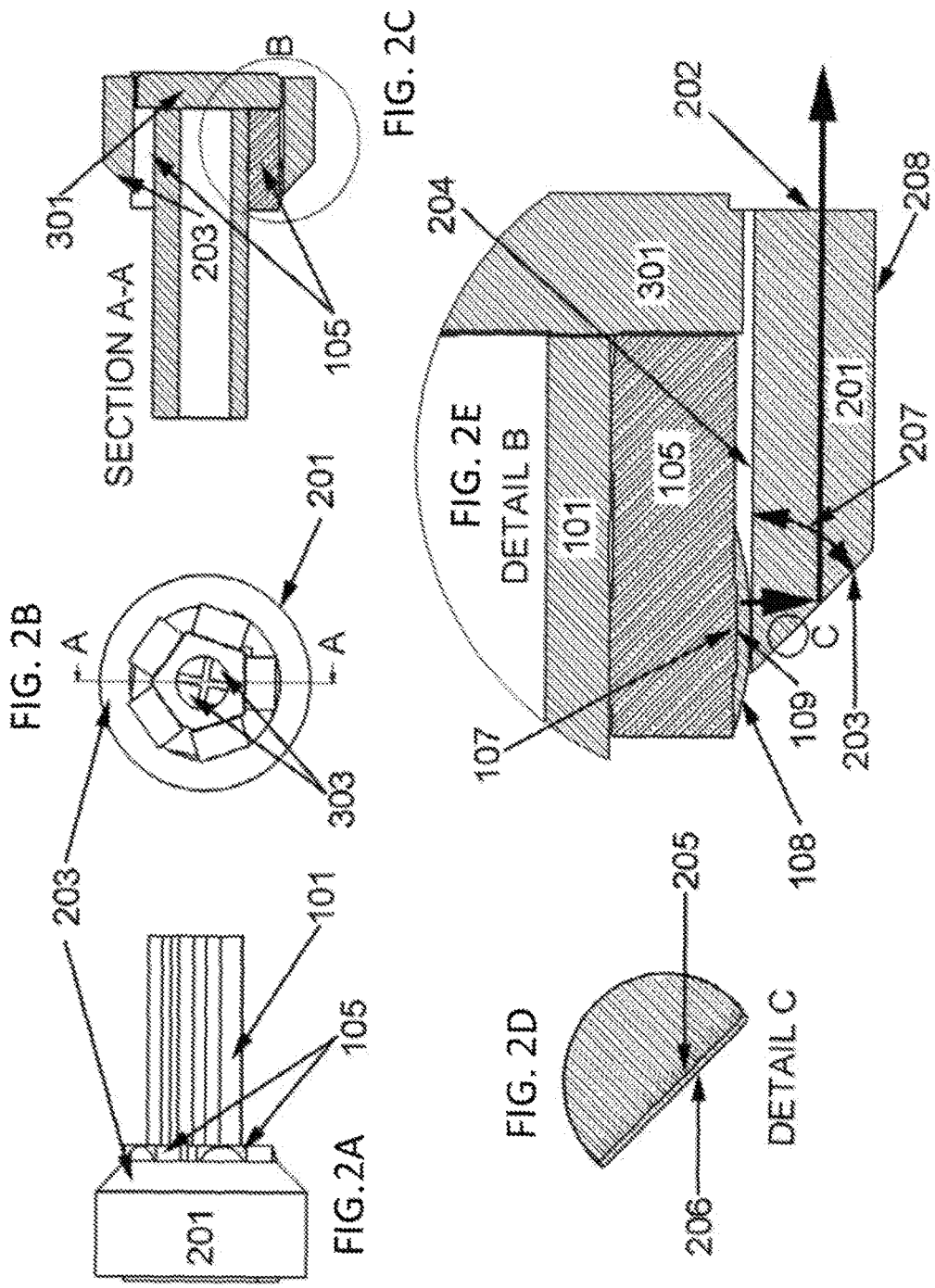

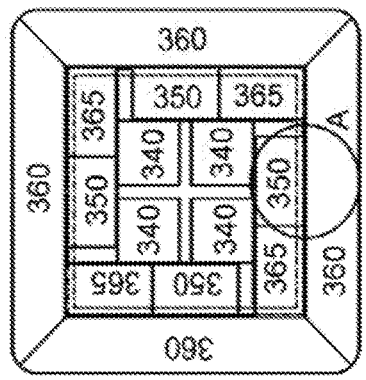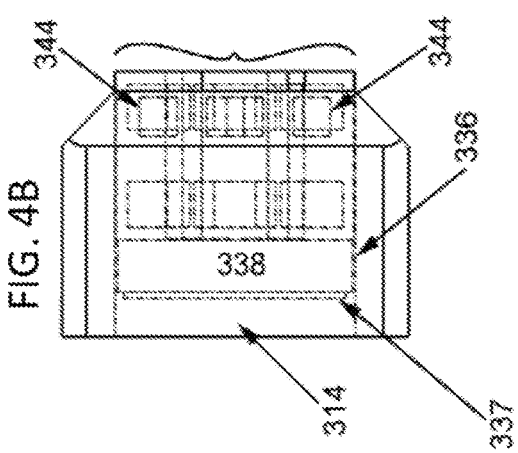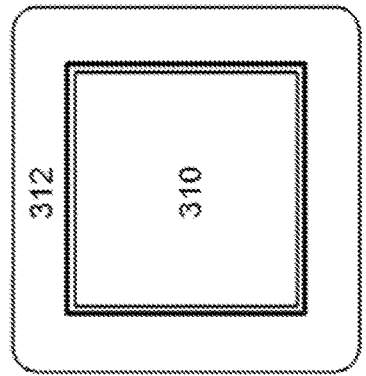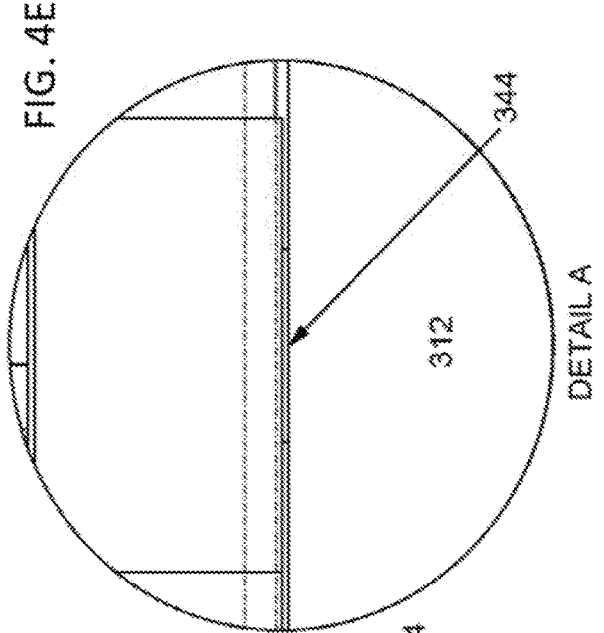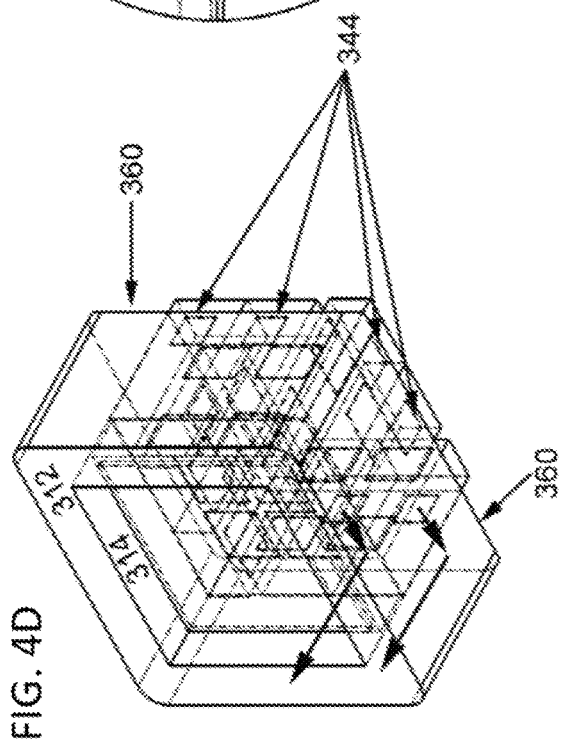

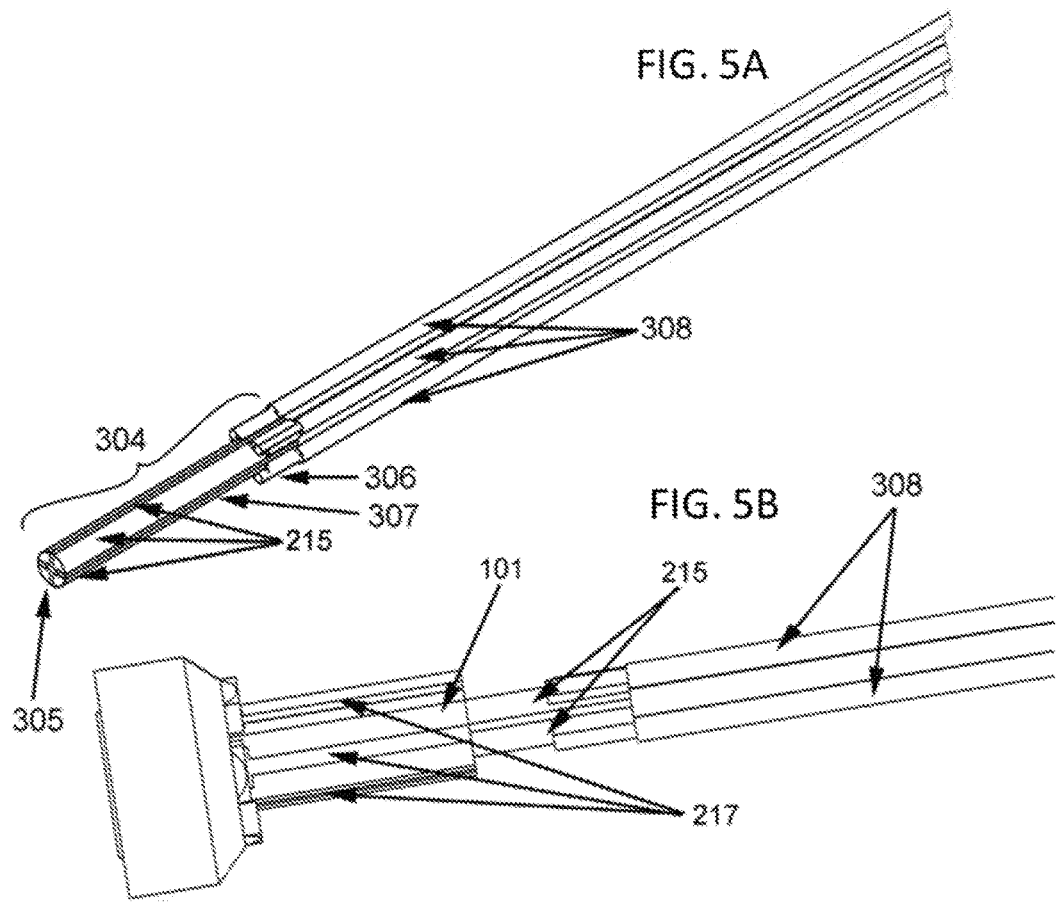
FIG. 5A
FIG. 5B
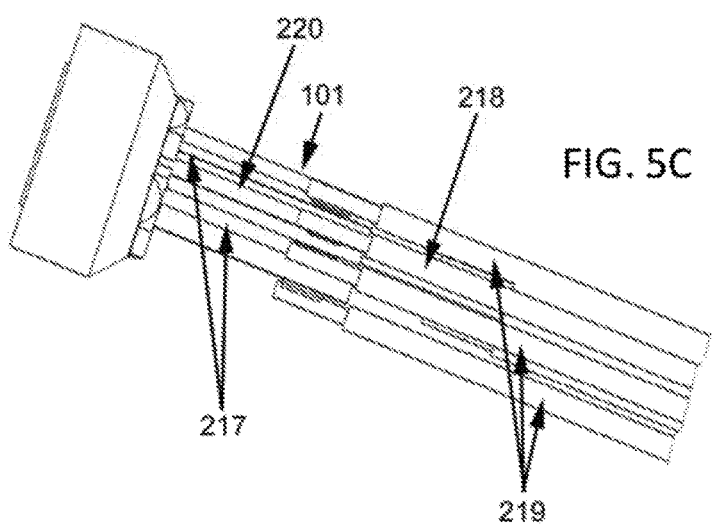
FIG. 5C

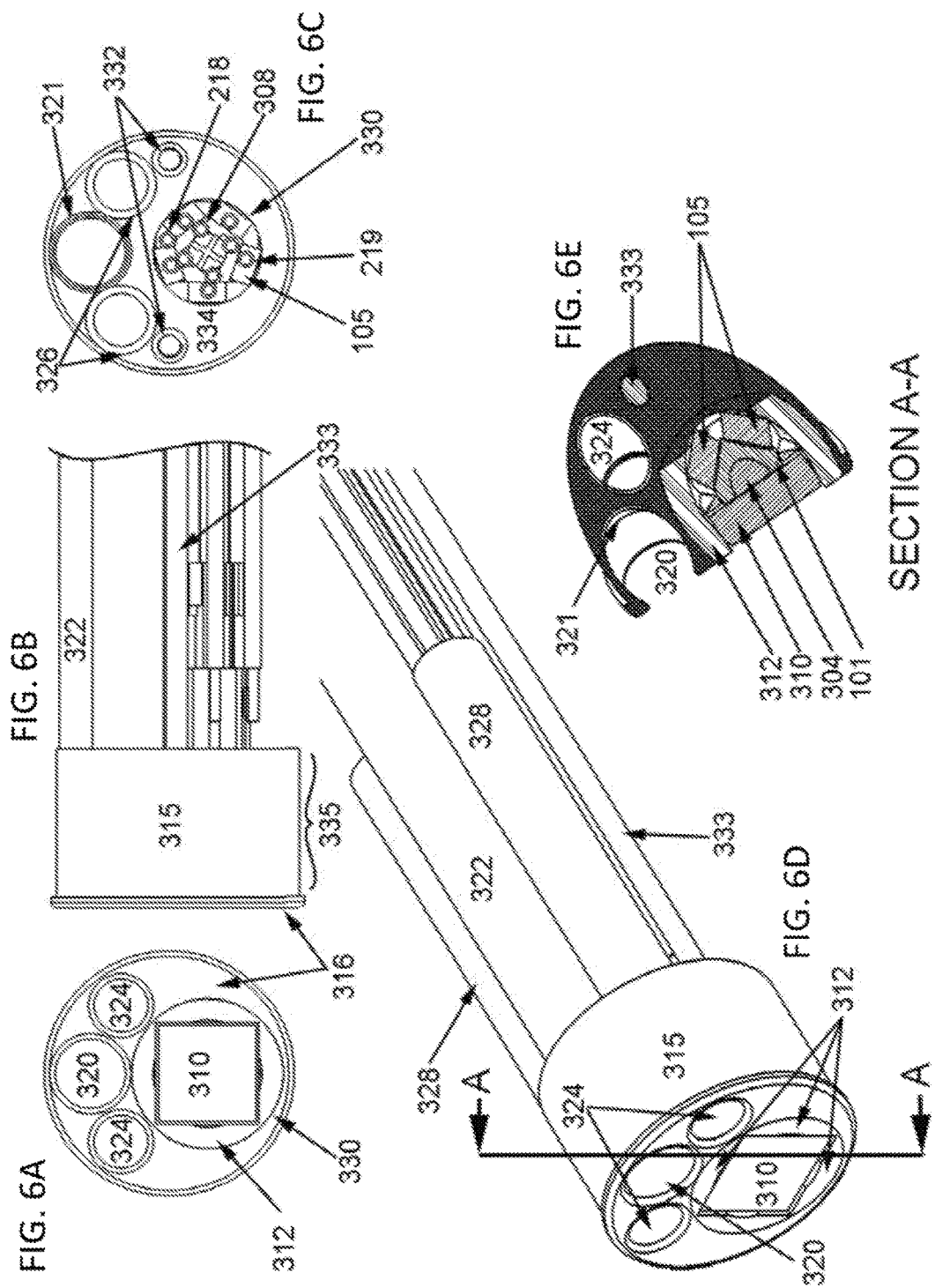

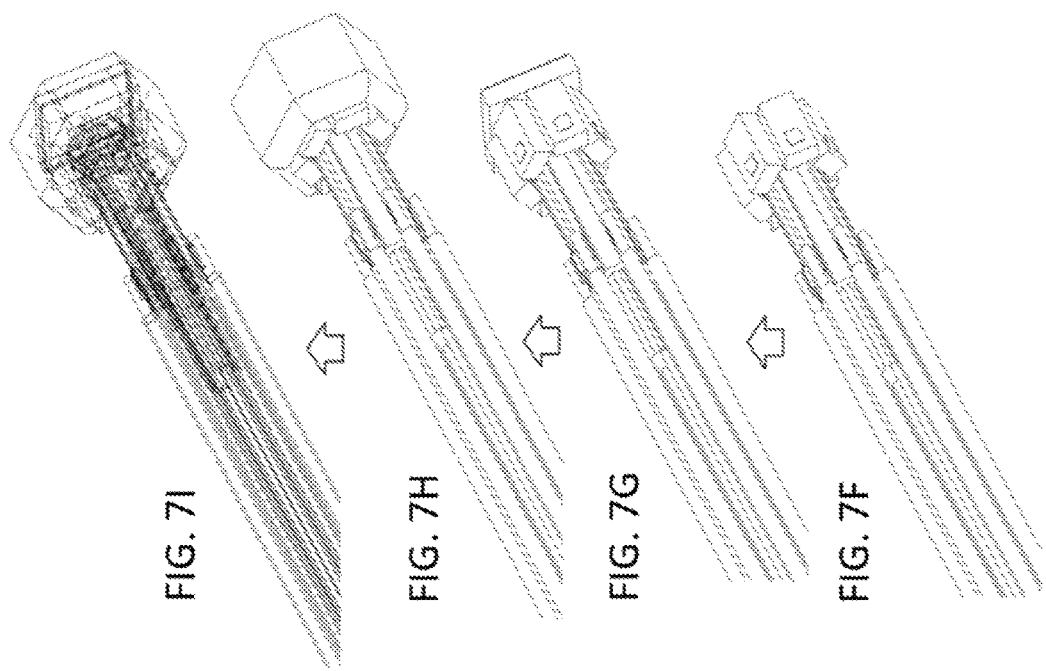
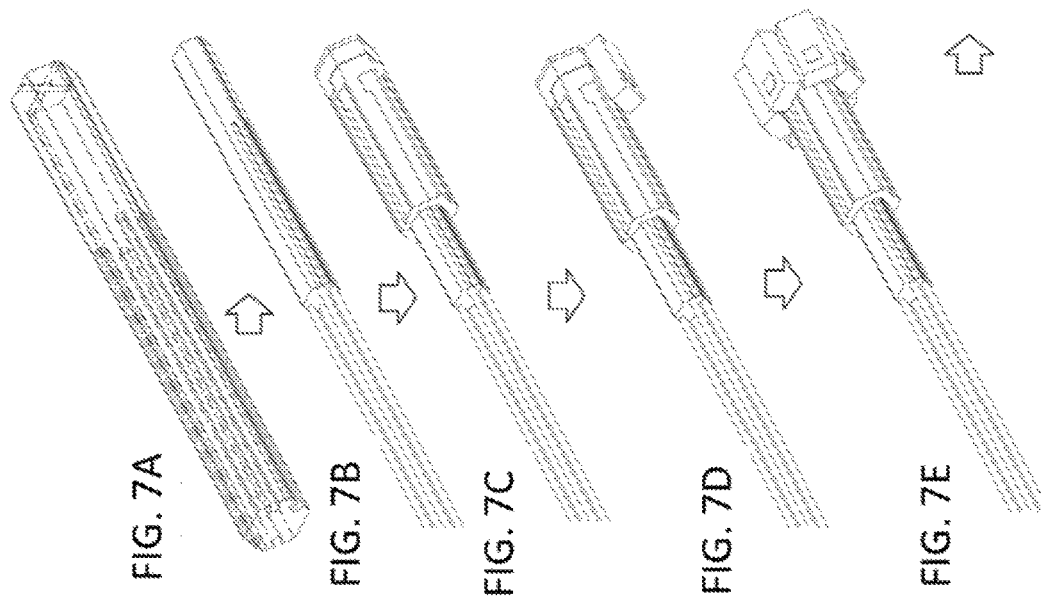
FIG. 7A
FIG. 7B
FIG. 7C
FIG. 7D
FIG. 7E
FIG. 7F
FIG. 7G
FIG. 7H
FIG. 7I

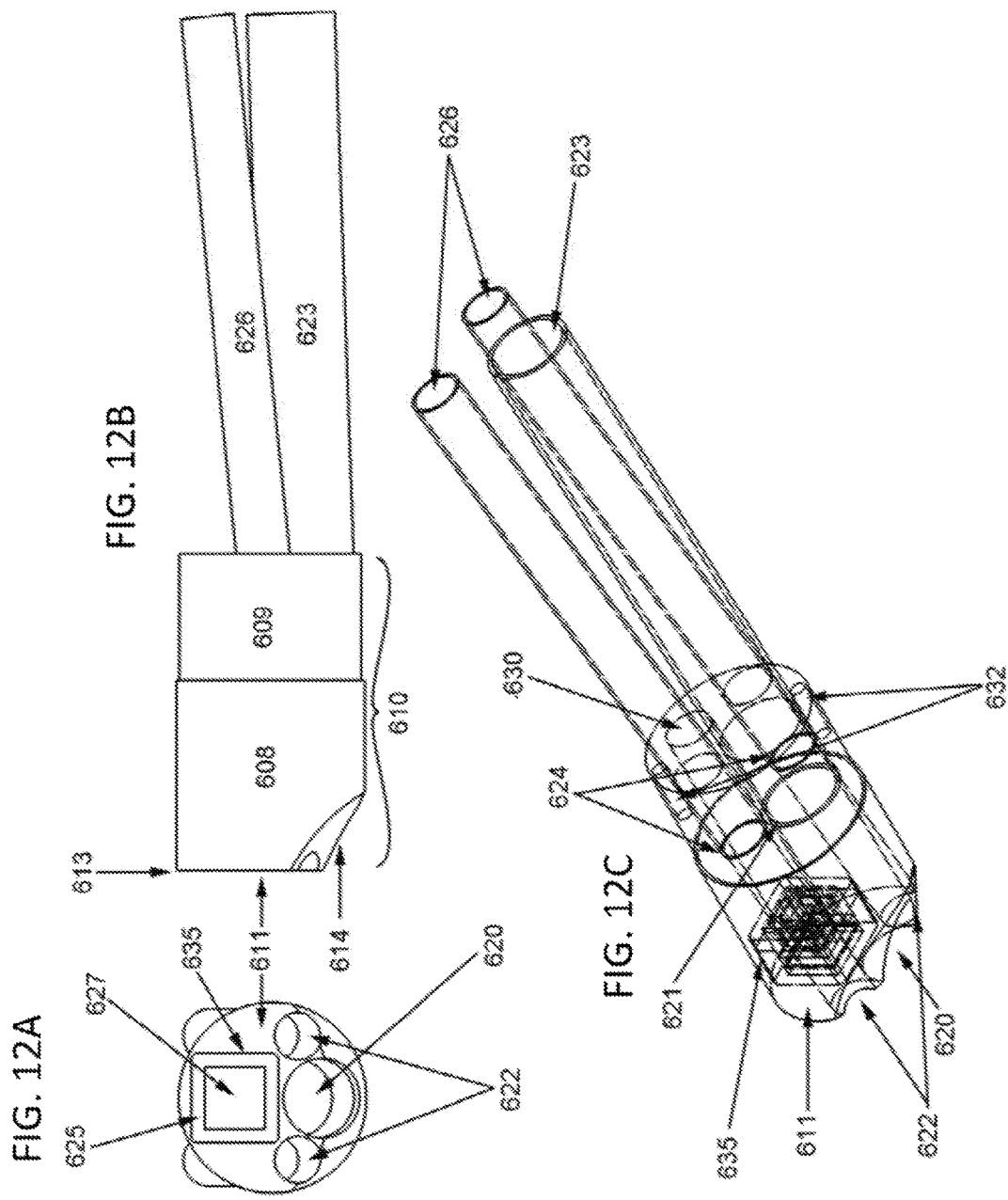

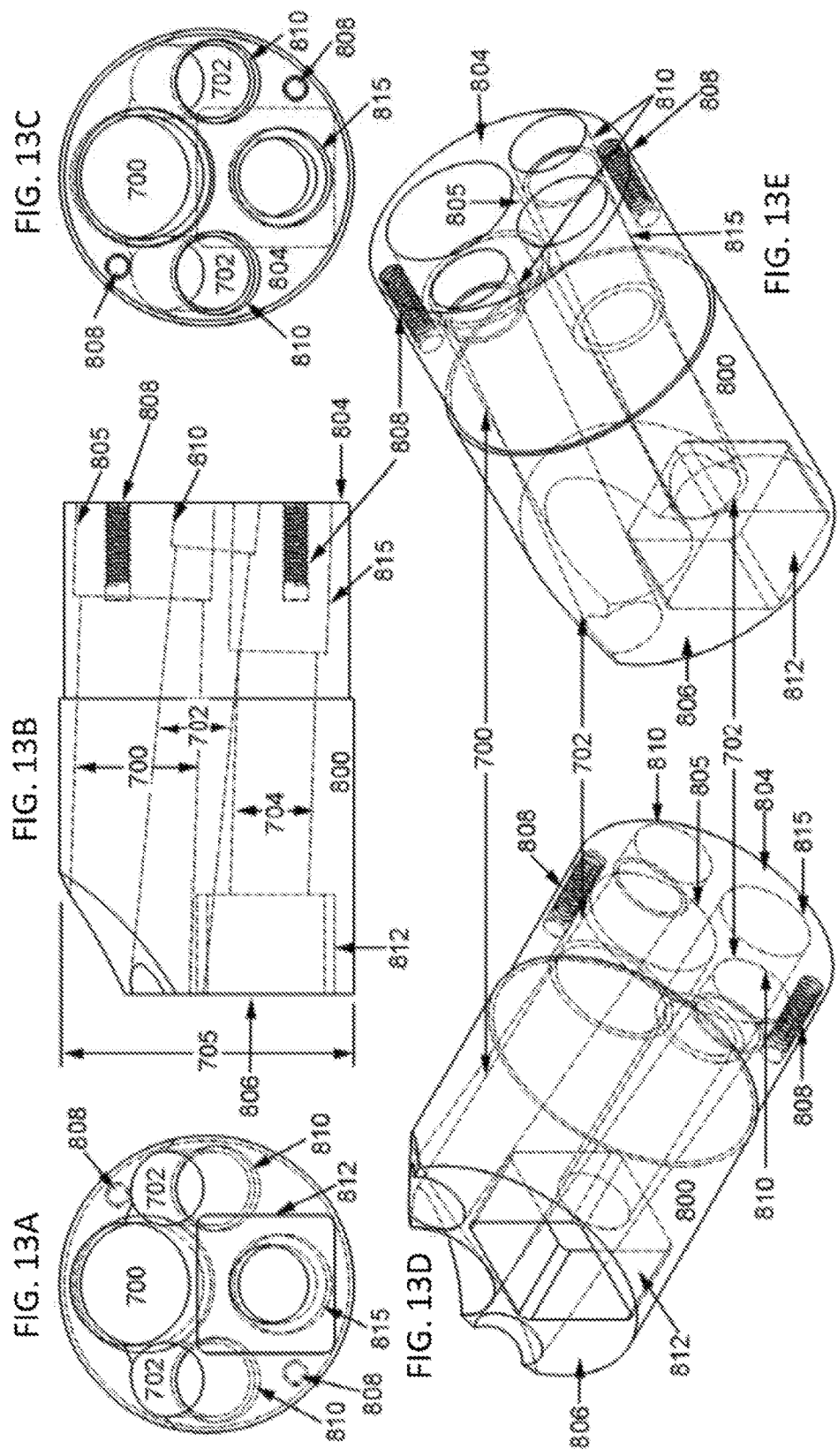

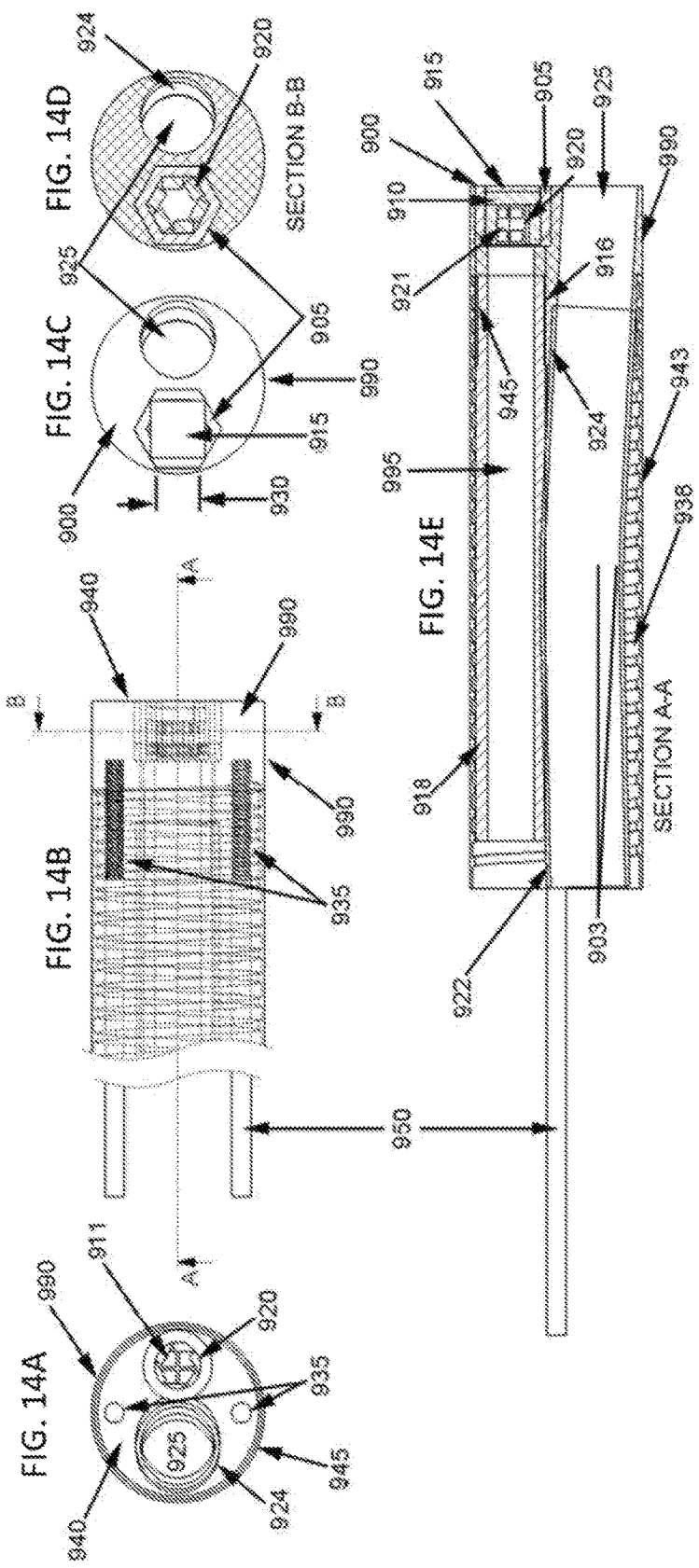

IN-VIVO IMAGING AND ACCESS SYSTEM UTILIZING A CANTED WORKING CHANNEL AND A RING ILLUMINATED SURGICAL CAMERA

FIELD OF THE INVENTION

Embodiments of the present invention generally relate to medical devices, medical catheters with steering and/or optical capabilities. Other embodiments are generally related to medical systems, such as in-vivo irrigation, illumination and visualization systems, that are suitable for viewing and/or performing diagnostic and therapeutic modalities within the human body, such as in the renal calyx or biliary tree.

BACKGROUND

A challenge for the minimally invasive exploration and treatment of internal areas of the human anatomy continues to be adequately visualizing the area of concern. Visualization can be especially troublesome in minimally invasive procedures in which small diameter, flexible and elongate instruments, such as catheters, endoscopes, or more specifically, ureteroscopes and duodenoscopes, are navigated through natural passageways of a patient to an area of concern, either in the passageway or in an organ accessible through the passageway.

Ureteroscopy is a procedure that is used to diagnosis and/or treat urinary tract diseases such as urinary calculi and ureteral strictures. An ureteroscope is inserted through the urinary tract and diagnosis and/or treatment occurs under direct visualization. Ureteroscopes are typically 2 mm to 3 mm (7 Fr. to 10 Fr.) diameter and include a sheath that encapsulates a fiber optic element, an illumination element and a working channel. Ureteroscopes provide a lumen for instrument access to tissue through the distal tip of the scope: a "working channel" or "forceps channel", permitting passage of devices, such as guidewires, optical fibers for delivery of laser energy and stone retrieval baskets. The working channel is also used for introducing sterile irrigant. Illumination is typically provided via an optical fiber bundle, terminated within the distal tip of the scope, transmitting light from a source outside of the body. Visualization is afforded via an imaging optical fiber bundle or, more recently, via a CMOS camera chip at the distal tip. Most ureteroscopes also incorporate a steering mechanism, which allows the distal tip of the scope to be deflected in one or more planes to follow the lumen with minimal trauma.

Prior art ureteroscopes/duodenoscopes are not disposable and require extensive, expensive maintenance and are costly to use and maintain for a variety of reasons. A scope must be cleaned and decontaminated/sterilized following each urological procedure (before reuse), potentially delaying successive procedures unless multiple scopes are available. Scopes suffer damage in use that ranges from scratches to working channel liners in passing instruments to a laser fiber burning through the side of the device, to broken steering mechanisms and require regular repair. Many ureteroscopes and duodenoscopes are incompatible with sterilization methods readily available in surgical centers. Decontamination or sterilization delays and costs associated with purchasing and/or repairing scopes have escalated the costs for ureteroscopic and other medical procedures that utilize similarly configured devices.

Illumination and imaging fiber optic bundles are frequently damaged prior to a scope being taken out of service, reducing the quality of direct visualization available between repairs, prolonging surgery and risks to the patient. Direct visualization may also be compromised with a fully operational scope, where irrigation flow is inadequate for removal of surgical detritus, as is the case when inserted instruments block a considerable portion of the working channel lumen. Scopes that cannot be sterilized between uses (and even those that can be and are sterilized) add a risk of infection, such as the famous Olympus TJF-Q180V duodenoscope cross-contamination cases (circa ~2008 to 2016).

A high degree of flexibility (or "deflectibility") and minimal diameter at and near the scope tip are prized characteristics for many surgical procedures. Fiber optic bundles occupy considerable space within the scope diameter and are expensive to maintain. Alternatives that eliminate the illumination and imagining fibers permit reduction of scope diameter, reduced resistance to deflection (and therefore smaller deflection wires), and thus offer a potential for provision of separate irrigation and working channels for reproducible surgical filed clearance.

Prior art devices use fiber optics for either illumination or visualization or both. The complexity and cost of devices using fiber optics for at least visualization has been precluded single use in flexible endoscopy. Early solutions for single use sought to minimize the cost by making the patient contacting portion of the scope disposable while reusing the scope handle/control section. The first flexible endoscope to be marketed as single use, Boston Scientific's LithoVue™, utilizes a CMOS camera chip and Light Emitting Diode (LED) to reduce costs, but the overall diameter of the tip remains relatively large at 3.2 mm (10.8 French) and the 3.6 Fr (1.08 mm bore) working channel must also deliver sterile irrigant and drain surgical detritus. The single illumination LED is adequate for most surgical applications, but its position adjacent the camera chip produces non-uniform lighting that lacks flexibility in illumination conditions useful in some surgeries.

It would be useful to provide a small diameter, flexible ureteroscope or duodenoscope or similar device that provides superior illumination and visualization with adequate irrigation and instrument access, within a single use package. Devices would be provided as sterile, reducing infection risks, for safe disposal following the procedure.

SUMMARY

In accordance with aspects of the present invention, a single use visualization system for use in medical procedures is provided. The system includes an endoscopic tube for insertion into the body, connected proximally to an endoscopic handle and extending distally for a length suitable for the biological lumen to be traversed. The endoscope handle provides access ports for various lumen within the overall endoscopic tube: a forceps port for accessing the forceps channel (aka the working channel, aka the catheter channel), through with irrigation flow may be directed in either direction, depending upon embodiment and mode of operation, and an irrigation port (or ports) for providing irrigant to one or more irrigation lumen in addition to, or in place of, irrigation within the forceps channel. An imaging system is located at or near the distal terminus of the endoscopic tube and includes an integral, compact illumination mechanism. The imaging system is further comprised by an image transmission cable and an electrical power conductor where the imaging system is provided with power from the proximal handle and delivers an image, located distal to the distal tip of the endoscopic tube, to the proximal end of the endoscopic tube. Power may be provided the proximal end of the image/power conductors directly from the handle or external to the handle.

A first embodiment of the endoscopic device is a diagnostic and/or surgical device that includes an endoscopic tip having a distal face, a longitudinal axis running from the distal face to a proximal end; a working channel and a RISC lumen; the distal face including a RISC counter bore and a distal end of the working channel; the working channel having a working channel longitudinal axis that is non-parallel to the endoscopic tip longitudinal axis.

A second embodiment is a device that includes a ring illuminated surgical camera that includes a ring lens that includes an emission surface, a reflector, and external surface, a lumen defined by an internal surface which extends longitudinally from the emissions face to the reflector, and an electric wire conduit port passing through the emissions face and adapted to carry an electronic imaging sensor and imaging sensor electrical contacts; a plurality of light emitting diodes (LEDs) carried within the lumen, adjacent to the internal surface of the ring lens, and adapted to radially emit light; an electronic imaging sensor adjacent to the emission surface, the electronic imaging sensor having an imaging array and imaging sensor electrical contacts; and a plurality of imaging sensor electrical contacts in electrical contact with the electronic imaging sensor passing through the electric wire conduit port and through the ring lens; the ring illuminated surgical camera carried in a recess of an endoscopic tip; the endoscopic tip affixed to a endoscopic cannula; the endoscopic tip including at least one working channel having a working channel longitudinal axis that is non-parallel to an endoscopic tip longitudinal axis; the at least one working channel affixed to a working channel cannula which is carried within the endoscopic cannula; and a plurality of guidewires affixed to the endoscopic tip, carried within the endoscopic cannula, and adapted to affect the orientation of the endoscopic tip.

BRIEF DESCRIPTION OF THE FIGURES

For a more complete understanding of the disclosure, reference should be made to the following detailed description and accompanying drawing figures wherein:

FIG. 2 shows a plurality of views and expanded views of a ring illuminated surgical camera where FIG. 2A shows an end-on view, FIG. 2B shows a side-on view, FIG. 2C shows a bisected view running along a longitudinal axis (the bisect shown in FIG. 2B as the line A-A), FIG. 2E is an expanded view of Detail B in FIG. 2C, and FIG. 2D is an expanded view of detail C shown in FIG. 2E;

FIG. 4 shows a plurality of views and expanded views of a square, ring illuminated surgical camera where FIG. 4A shows on end-on view, FIG. 4B shows a transparent side view, FIG. 4C shows a rear view of with the LED support removed but the LEDs remaining, FIG. 4D shows a transparent orthogonal projection depicting the path of light from the LEDs to the emission surface, and FIG. 4E shows an expanded view of Detail A in FIG. 4C;

FIG. 5 shows a stepwise assembly of a ring illuminated surgical camera and leads, where FIG. 5A shows the contact post and camera leads, FIG. 5B shows the contact post fitted into the LED support which is carrying LEDs and a ring lens, and FIG. 5C shows the LED contacts connected to the LED support;

FIG. 6 shows a plurality of views of a ring illuminated surgical camera incorporated into an endoscopic device where FIG. 6A shows an end-on view of the endoscopic device's tip with working channels, FIG. 6B shows a side view of the endoscopic tip, FIG. 6C shows a rear view of the endoscopic tip with guide wire contact posts and electrical leads, FIG. 6D shows an orthogonal projection of the endoscopic tip, and FIG. 6E shows a bisected, off-axis view of the endoscopic tip (the bisect shown in FIG. 6D as the line A-A);

FIG. 7 shows a stepwise construction of a ring illuminated surgical camera starting from the camera contact post in FIG. 7A, adding camera leads in FIG. 7B, adding the LED support in FIG. 7C, adding a first LED in FIG. 7D, adding additional LEDs in FIG. 7E, adding LED leads in FIG. 7F, adding a camera in FIG. 7G, and adding a ring lens in FIG. 7H, where FIG. 7I is a transparent orthogonal projection of the ring illuminated surgical camera;

FIGS. 9A, 9C & 9D, and 9E, show an end-on, two side views, and a rear view of the working-channel ring lens, respectively, and where FIGS. 9B and 9F show an orthogonal front and an orthogonal rear projection of the working-channel ring lens, respectively;

FIG. 10A shows a side view of the ring lens, FIG. 10B shows a transparent side view of the ring lens, FIG. 100 shows a bisected view of the ring lens (the bisect shown in FIG. 10B as the line A-A), FIG. 10D shows an rear view of the ring lens carrying LEDs, FIG. 10E shows a top-down orthogonal projection of the ring lens, and FIG. 10F shows a bottom-up orthogonal projection of the ring lens carrying LEDs;

FIG. 12 shows an end view FIG. 12A, a side view FIG. 12B, and an orthogonal projection FIG. 12C of an endoscopic tip;

FIG. 13 shows a distal end view FIG. 13A, a side view FIG. 13B, a proximal end view FIG. 13C, a proximal, orthogonal projection FIG. 13D, and a distal, orthogonal projection FIG. 13E of an endoscopic tip; and FIG. 14 shows a proximal end view FIG. 14A, a top view FIG. 14B, a distal end view FIG. 14C, a radial cross-sectional view Fib 14D, and a longitudinal cross-sectional view FIG. 14E of an endoscopic tip.

While specific embodiments are illustrated in the figures, with the understanding that the disclosure is intended to be illustrative, these embodiments are not intended to limit the invention described and illustrated herein.

DETAILED DESCRIPTION

Objects, features, and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

Herein, the use of the word "a" or "an" when used in conjunction with the term "comprising" in the claims and/or the specification may mean "one," but it is also consistent with the meaning of "one or more," "at least one," and "one or more than one." The term "about" means, in general, the stated value plus or minus 5%. The use of the term "or" in the claims is used to mean "and/or" unless explicitly indicated to refer to alternatives only or the alternative are mutually exclusive, although the disclosure supports a definition that refers to only alternatives and "and/or."

Herein are provided components for and a structure of a ring illuminated surgical scope. The components and structure include a Ring-Illuminated Surgical Camera (RISC) that features at least one light emitting diode (LED), a ring lens, and an electronic imaging sensor. The components and structure provide circular or ring illumination of an optical target thereby allowing the user to clearly image/see the optical target. Importantly, the organization of the LED, ring lens, and imaging sensor in the RISC decrease the cross-sectional diameter of a surgical scope while providing improved diagnostic or surgical capabilities.

A first embodiment of a RISC includes one or more LEDs positioned behind, rather than in plane with, an electronic imaging sensor. Herein, the terms electronic imaging sensor, camera, and camera array mean an electronic device that is adapted for the conversion of light to electrical signals that can be converted back to an image. Examples of such electronic devices include CMOS sensors and CCD sensors.

Figure 1A:
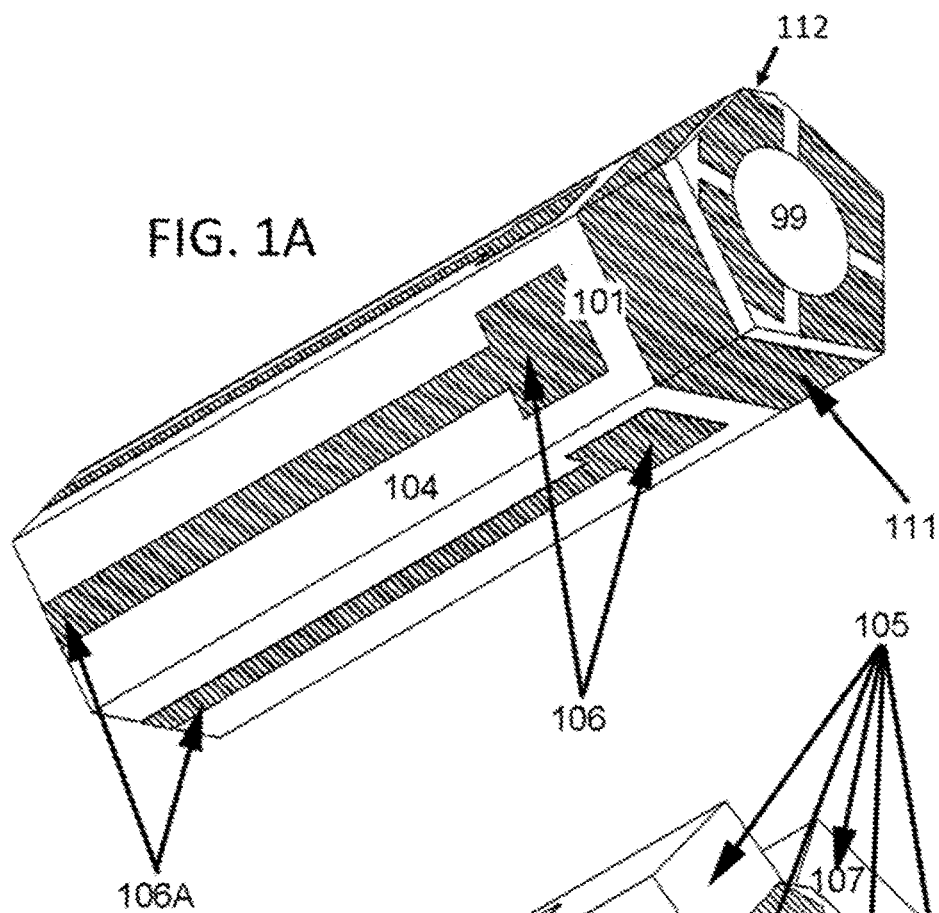
FIG. 1 shows a LED stack with exposed electrodes (FIG. 1A, the LED support) and with affixed LEDs (FIG. 1B)
Figure 1B:
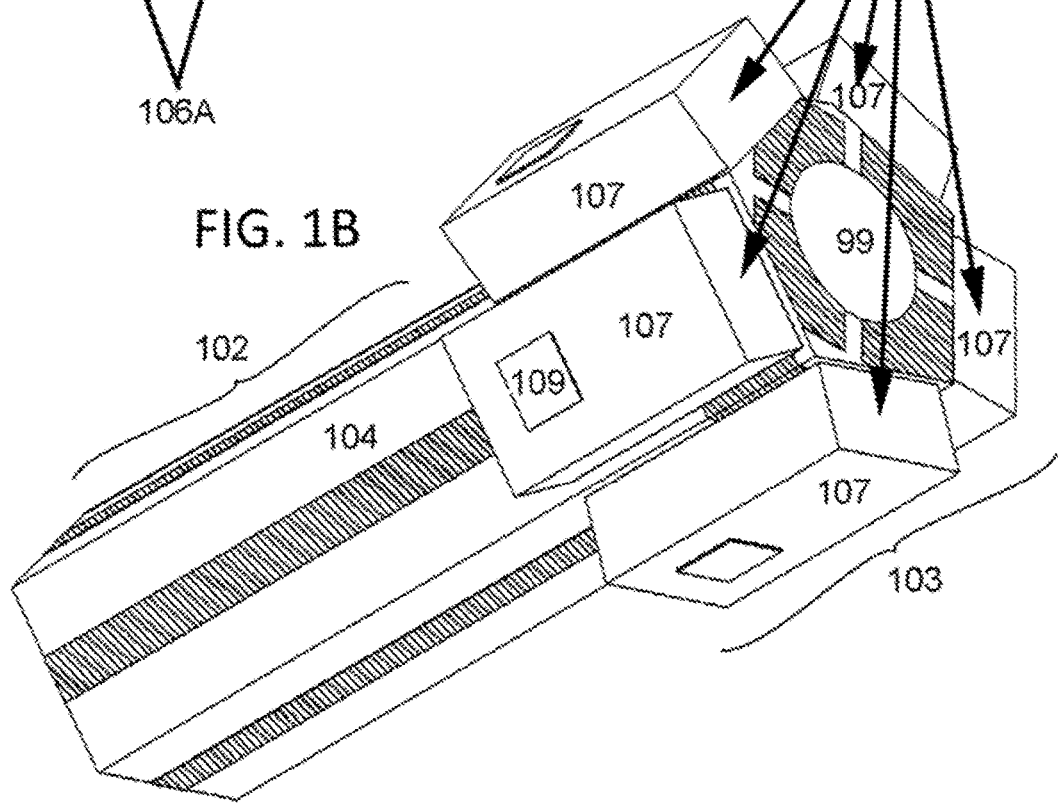

With reference to FIG. 1 (A and B), herein is provided a compact arrangement of a plurality of LEDs 105, each having a LED emitter 109 upon the substrate 107 and positioned behind and non-parallel with an imaging sensor (not shown). The LED stack includes an LED support 101 and affixed thereto a plurality of LEDs 105. The LED support 101 (FIG. 1A) includes a plurality of support faces 104 each carrying at least one LED power contact 106 and a length of a common return contact 111. The LED support 101 can have 3, 4, 5, 6, 7, 8, 9, or 10 support faces 104, that is, the LED support can have a triangular, square, pentagonal, hexagonal, heptagonal, octagonal, nonagonal, or decagonal cross-section. While additional support faces are possible (in excess of 10), the LED support 101 is preferably sufficiently narrow to allow for use in surgical scopes. Preferably, the LED support 101 has a square, pentagonal, or hexagonal cross-section; that is, the LED support 101 preferably has 4, 5, or 6 support faces 104. Each support face, preferably, further includes at least one LED contact 106 electrically connected to an LED lead 106A and a LED return/common/ground or common LED ground 111. The common LED ground 111 can be carried across a plurality of support faces 104. In certain instances, the LED support 101 can have a plurality of support faces 104 and a LED ground face 112. The LED ground face 112 can have the same dimensions as a support face 104 or can have a more narrow width (whereas the length is preferably the same as the support faces). For example, FIG. 1A depicts an irregular hexagonal cross-section where the LED support 101 has five (5) common faces and a narrower LED ground face 112. When the LED support 101 has a LED ground face 112 the common LED ground 111 is preferably carried across each support face 104 and the LED ground support face 112 (e.g., wrapped around the LED support 101). In a common instance, the LED contact 106, the LED lead 106A, and the common LED ground 111 are composed of a conducting metal, preferably copper, silver, or gold.

The LED support 101 preferably carries at least one LED 105 on each support face 104. Each LED 105 has a LED emitter 107. The LED emitter 107 (or chip or die) commonly has a flat or planar surface and emits light perpendicular to the planar surface (primary emission direction). Preferably, this primary emission direction is non-parallel to the LED support 101 longitudinal axis. More preferably the LED emitter 107 (herein defined by its planar surface) is preferably planar with the support face 104 upon which the LED 105 is affixed. Each LED 105 is preferably affixed (e.g., soldered) to a LED contact 106 and a LED ground 111.

In another instance, the LED support 101 includes a proximal region 102 and a distal region 103. Preferably, the LEDs 105 are carried on (affixed to) the distal region 103 with the LED leads 106A extending to the proximal region. The distal region 103, preferably, includes the LED contacts 106 and the common LED ground 111.

In reference to FIG. 2, each LED 105 can further include a lens or a shaping lens 108 carried or covering the LED emitter 107 and the LED emitter's emission face 109. Preferably, the lens 108 directs light (emissions) from the LED 105 into a ring lens 201 positioned about the LED support 101 and the LEDs 105. As depicted in FIG. 3E, light (large arrows) from the LEDs 105 travels from the emission face 109, through the lens 108, into the ring lens 201. Preferably, the ring lens 201 is adapted to reflect or redirect the light from the LED 105 to and out of an emission surface 202. In one instance, the ring lens 201 includes a ring-shaped body; notably, while the lens is a ring lens, the lens is not required to possess circular symmetry. The ring lens 201 can be circular or possess the same number of sides as the LED support 101. In one preferable instance the ring lens is circular. The ring lens preferably includes an internal surface 204, an external surface 208, a reflector surface 203, and an emission surface 202. In operation, light entering the ring lens 201, preferably, transmits through the internal surface 204, to the reflector surface 203, and exits the ring lens 201 through the emission surface 202. In one instance, the reflector surface has an internal 205 and external 206 components (or surfaces). The reflector surface 203 is angled relative to the internal surface 204 (or the longitudinal axis of the LED support 101). The reflector surface can be at an angle 207 of about 35° to about 55°. In one instance, the reflector surface is angled to provide a total internal reflectance (TIR) of light from the LED 105 to the emission surface 202. In another instance, the reflector surface (the external component 206), ring lens internal surface 204 and ring lens external surface 208 can be mirrored to improve the reflectance and redirection of the light within the ring lens 201. The device includes a plurality of LEDs, the emissions can blend producing uniform illumination about a camera array 301.

Figure 3:
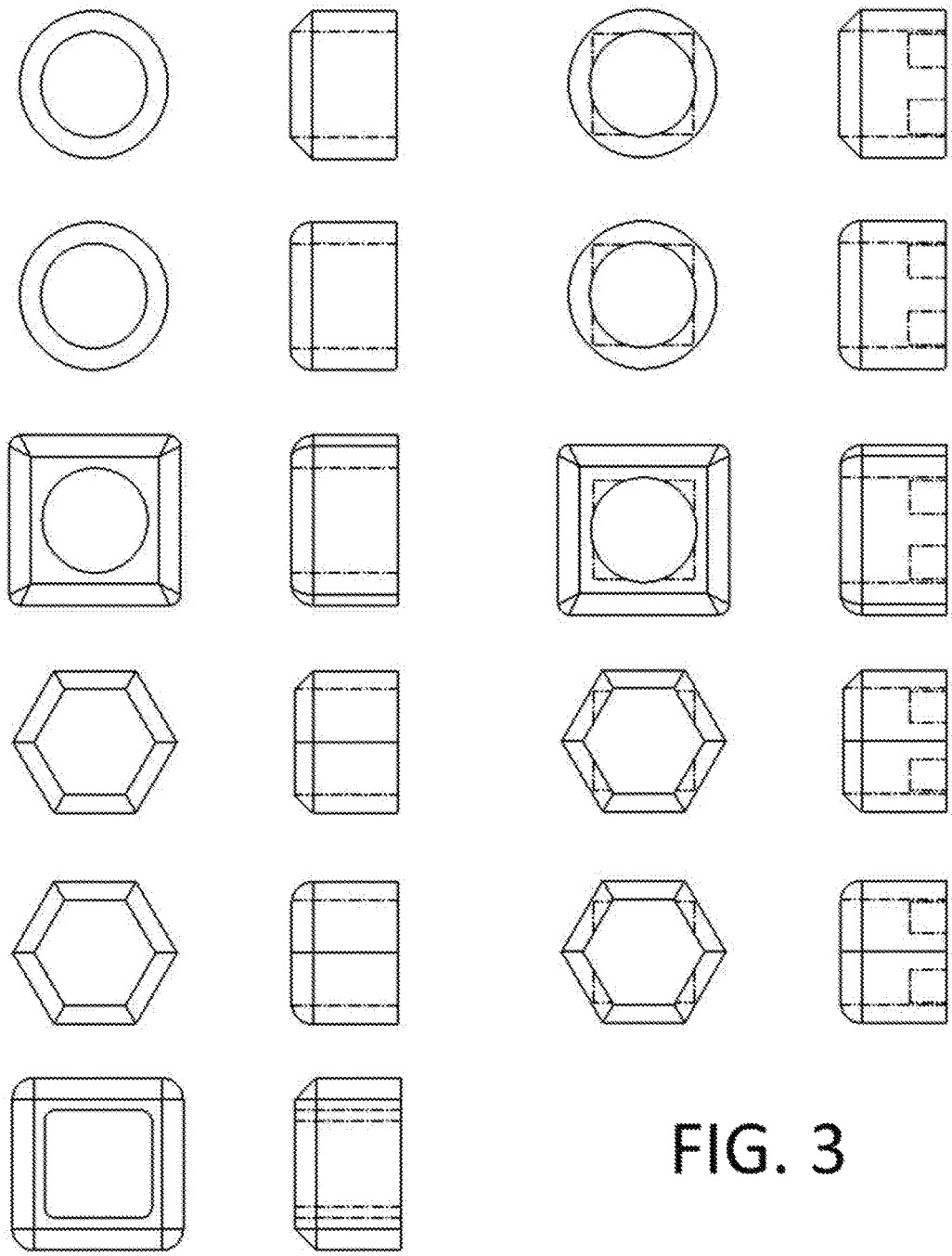
FIG. 3 depicts a series of ring lenses having a variety of shapes, chamfered or filleted geometries, and recesses for carrying an imaging element.

In another example, FIG. 3 the ring lens can have a cross-section that is round, square, pentagonal, or hexagonal. In these examples, the ring lens can have a camera countersink (adapted to carry the camera array). Notably, the proximal end of the ring lens can have a chamfered or filleted geometry. In one instance, the ring lens includes an external surface that is mirrored. In still another example, the ring lens includes an emissions face (where the light from the LEDs exits the ring lens). In a preferable example, the emissions face can be planar. In other examples, the emissions face can be convex, concave, convex conical, or concave conical. Notably, the selection of the orientation of the emissions face can be dependent on the number of LEDs, the focal point of the LEDs and the camera array, and any tools that are used in a surgical space. In a preferably example, the ring lens is a unitary piece of fused silica or quartz.

FIG. 4 depicts another example of the RISC without showing the LED support or the imaging contact post. In this example, the ring lens 312 has a square profile. Furthermore, in this example, the ring lens does not include a countersink, but the inside diameter of the ring lens is approximately the same diameter of the camera array, for example, within about 0.01, 0.02, 0.03, 0.04, 0.05, 0.06, 0.07, 0.08, 0.09, or 0.1 mm of the diameter of the camera array. Here, the camera array 310 rests within the open internal cross-section (lumen, meaning the inside space of a tubular structure) 336 of the ring lens 312. The camera array can be set back (proximal) beneath a window 314 used to seal the sensor space and protect its surface. In another instance, the camera array can be flush with the emission surface of the ring lens. In yet another instance, the ring lens 312 and the window 314 can be a single piece of transparent material, e.g. fused quartz, fused silica, sapphire, polymer, crown glass, where the volume for the camera array is provided within the single piece of transparent material.

The camera array 310 can include a chip 337 and a substrate 338 upon the proximal side of which are provided camera electrical contacts 340. The camera electrical contacts 340 are preferably in electrical contact the electrical contacts 305 for the camera array, or traces 215 (FIG. 5A & FIG. 5B), carried on the contact post 304 (FIG. 5A). In one instance, the chip 337 (or chip face) is adjacent to, or in contact with the window 314.

As shown in FIG. 4, the RISC can include a plurality of LEDs wherein the plurality of LEDs can be grouped or individually distinct by wavelength or wavelength range. FIG. 4C depicts eight LEDs in two groups of four (350 and 365). Preferably, the RISC includes at least 3, 4, 5, or 6 "white" light LEDs 350 symmetrically placed about the ring lens 312. Herein, symmetrically placed can mean that there is a rotational axis along the longitudinal axis. Preferably, symmetrically placed means that when the "white" light LEDs are actuated and providing illumination about the camera array, the resulting projected light is symmetric. The RISC can further include auxiliary LEDs 365 that can provide light in one or more colors. Preferable examples include providing blue or red light to accentuate blood vessels, UV light to stimulate fluorescent dyes, or light of different color temperatures to provide alternative lighting or contrast when the surgical field is viewed via the camera array.

FIG. 4D depicts light (large arrows) exiting the LED emitters 344, entering the ring lens 312, being reflected by the angled TIR or mirror surface 360, and then exiting about the camera array 310. In contrast to prior art, such arrangements provide several fold more light in the surgical field and that light is far more uniformly distributed about the imaging element while requiring less space within the endoscope tip than other arrangements.

In another instance, the LED support includes a bore 99 (FIG. 1) or pathway from the proximal end to the distal end through which an imaging contact post 304 (FIG. 5) can be passed, preferably without contacting the LED contacts 106 or LED leads 106A (FIG. 1). Preferably, the imaging contact post 304 fits the bore though the LED support 101, that is has approximately (within about 0.05 mm) the same dimensions as the bore and can be pressed into position during assembly. In another instance, the bore and the contact post 304 have a cross section that is similar or the same as the LED support 101, e.g. square, pentagonal, or hexagonal. In one preferable instance, the contact post 304 has a square cross-section. In another preferable instance, the contact post 304 is cylindrical.

FIG. 5 depicts the LED support 101 carrying the ring lens 201 with the contact post 304 and shows the electrical contacts for both the LED and the camera array. The electrical contacts for the camera array, or traces 215, are preferably carried on the face 307 of the contact post 304. As shown in FIG. 5A, the contact post carries both the traces 215 and camera conductors 308. The camera conductors 308 are in electrical contact with the traces 215, preferable are affixed to the traces 215, more preferably are soldered 306 to the traces 215. The conductors 308 can be standard electrical wires or a bundle of insulated wires fitted about at least a portion of the contact post 304 or coaxial shielded cable. FIG. 5B depicts the contact post 304 fitted within the LED support 101, preferably with a minimum distance of about 0.1, 0.2, 0.3, 0.4, 0.5, 0.6, 0.7, 0.8, 0.9, or 1 mm between the proximal end of the LED support 101 and the terminus of the camera conductors 308.

Another instance includes wiring for the LEDs 105. As shown in FIG. 5C, an LED conductor 219 is preferably in electrical contact with, more preferably affixed to, even more preferably soldered to a LED lead 217 (106A in FIG. 1). In one example, there is one LED conductor for each LED 105; in another example, there is wiring such that the LEDs 105 are in series or in parallel. In either example, a complete circuit requires a ground (return). Preferably, a common conductor 218 is in electrical contact with, more preferably affixed to, even more preferably soldered to the common LED ground 220 (111 in FIG. 1). In another instance, each LED 105 (FIG. 1) can be in electrical contact with a ground, or a plurality of LEDs 105 can be in electrical contact with a single ground. Preferably, there is one LED conductor 219 for each LED lead 217, thereby providing a means for individually and selectively activating (actuating/illuminating) each LED. A proximal end-on view of the arrangement of the LEDs 105, LED conductors 219, common conductor 218, and the camera conductors 308 is depicted within FIG. 6C.

In another instance, the RISC features the LEDs 105, LED support 101, the camera contract post 304, and the camera array 310, with the leads and grounds carried by the LED support 101 and the contact post 304. The RISC can then further include the LED conductors 219, common conductor 218, and the camera conductors 308 each in electrical contact with the LEDs, leads, grounds, or camera array. Alternatively, the RISC can include a ring light that features the LEDs 105 and the LED support 101 (as shown in FIG. 1) and a camera component that includes the camera array 310 and the contact post 304.

FIG. 6 further shows features and elements of the working end of an endoscope that includes a RISC. In one example, the scope tip body 315 includes at least one counter bore recesses (in the scope tip face 316) for mounting a RISC. The scope tip body 315 can further includes a working channel port 320 and counter bore 321 for mating the working channel liner 322, an auxiliary port 324 and counterbore 326 for mating with a conduit 328 (for example, for use in continuous flow irrigation or other needs), a RISC bore 330 for mounting the RISC assembly as depicted in FIG. 2; and a turned down region 335 having an exterior diameter for mating with an endoscopic outer sleeve/cannula (not shown).

In one embodiment of the RISC, the camera array can be square (most commonly the camera array is square due to the 2-dimensional grid design of the detecting elements, other shapes can be imagined). In one instance, the camera array is counter sunk into the ring lens. That is, the face of the camera array can be flush with the emission face 202 of the ring lens. In another instance, the face of the camera array can extend beyond the emission face 202 of the ring lens 201 (FIG. 2). In one example, the camera array is seated on the ring lens, in another example the camera array is within the internal diameter of the ring lens. FIGS. 4A and 4D depict a square, camera countersink 310 in the ring lens 312. In this example, the lens ring 312 is mounted within the scope tip body 315, with the emission surface 202 flush with the scope tip face 316.

The scope tip body 315 (FIG. 6) can further include steering wires 333 for control of the orientation of the scope tip face 316. The steering wires 333 can be mounted within receiving holes 332 provided on the proximal face 334 of the scope tip body 315. Notably, FIG. 6A shows an end-on view of the scope tip body 315 (in FIG. 6B) whereas FIG. 6C shows an internal view of the scope tip 315 (in FIG. 6B) as seen from the proximal end. Preferably, the steering wires and mounted to the scope tip body 315 within receiving holes 332 that do not extend through the scope tip body 315 to the scope tip face 316.

FIG. 6E shows a diagonal cross section of the scope tip body 315 depicted in FIG. 6D. Therein, portions of the LED support 101, LEDs 105, and sensor contact post 304 are visible. Other elements described in FIG. 2 may be seen in FIG. 6C for orientation: an LED 105, sensor conductors 308, LED power 219 and common/return 218 conductors.

Figure 8:
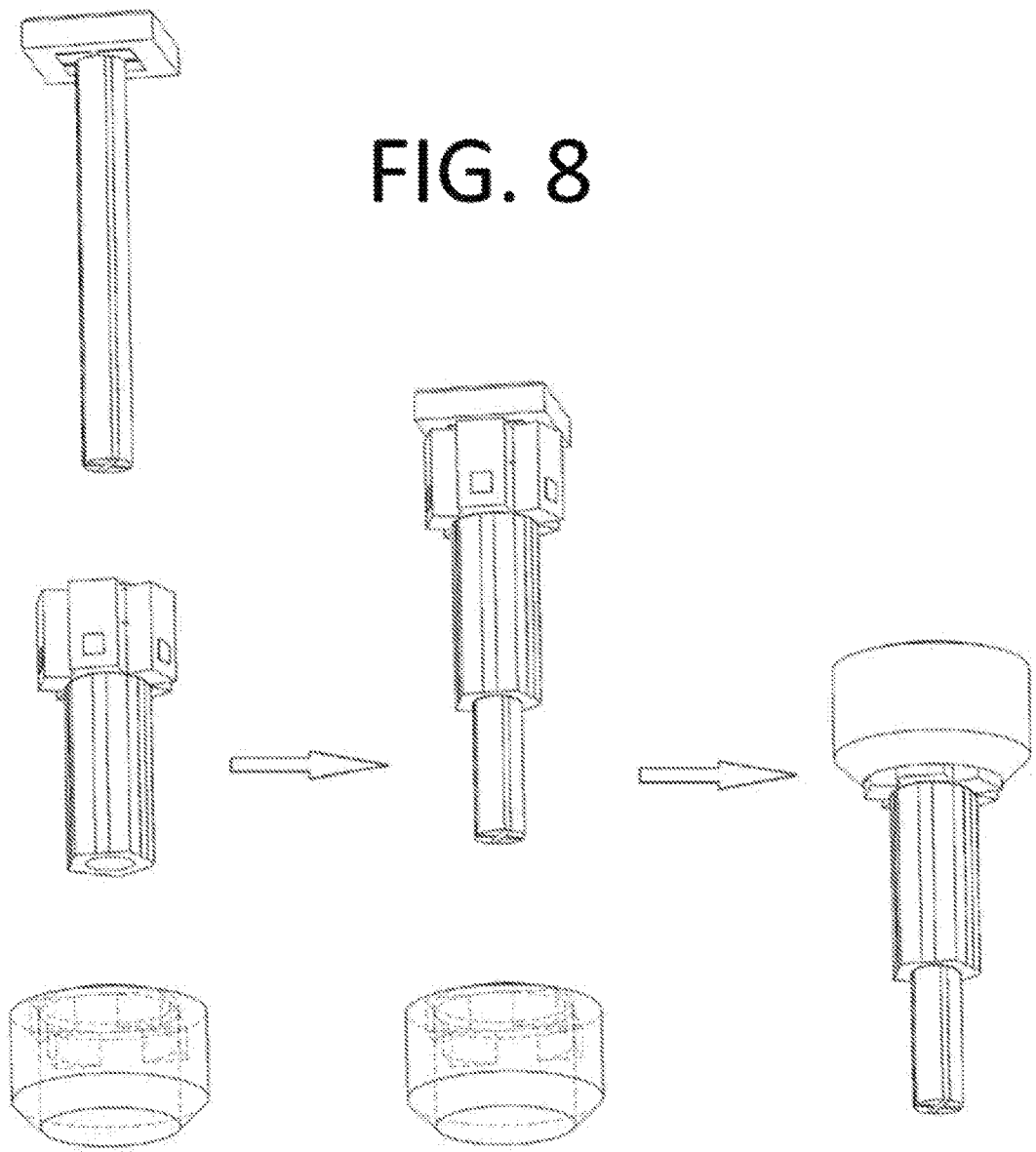
FIG. 8 shows a schematic assembly of a ring illuminated surgical camera, showing a placement of the camera on the camera contact post, the LED support carrying the LEDs, and the ring lens.

FIG. 7 shows another embodiment wherein the ring lens if hexagonal, illustrating a means for build-up of the RISC assembly. Notably, FIG. 7 shows a layer by layer arrangement of a ring illuminated surgical camera starting from the camera contact post in FIG. 7A. Then in FIG. 7B, camera leads are shown added to the camera post. Then the LED support in FIG. 7C is shown over the camera post. Next, in FIGS. 7D and 7E, LEDs are shown affixed to the LED support. Then in FIG. 7F, LED leads are shown connected to the LED support. In FIG. 7G, the electronic imaging sensor (camera) is shown in relation to the LEDs. FIG. 7H now shows the ring lens (a hexagonal ring lens) about the LEDs and electronic imaging sensor. Finally, FIG. 7I shows a transparent orthogonal projection of the ring illuminated surgical camera. Notably, the assembly of the ring illuminated surgical camera can follow the order shown in FIG. 7 or can follow an order determined by the means of assembly. In one notable instance, the electronic imaging sensor is added after the ring lens. In another instance, the leads are added after the assembly of the LED support, LEDs, camera post, and ring lens. Likewise, FIG. 8 shows and exploded assembly of the ring lens (i.e., a circular ring lens), the LED support carrying LEDs, and the camera post carrying the electronic imaging sensor.

A further embodiment of the ring illuminated surgical camera includes a LED support including a proximal region, a distal region, a plurality of external faces extending from the proximal region to the distal region, and a longitudinal axis extending from the proximal region to the distal region. The RISC further includes a plurality of light emitting diodes carried radially about the LED support and carried upon the external faces of the LED support. Additionally, the RISC includes a ring lens including an emissions face, a reflector, and an internal surface extending longitudinally from the emissions face to the reflector. Preferably, the plurality of light emitting diodes are adjacent to the internal surface of the ring lens. In one instance, the RISC includes 4 to 8 LEDs, in another instance, the RISC includes at least one LED for each common face on the LED support (See the discussion of FIG. 1A which depicts an irregular hexagonal cross-section where the LED support having five (5) common faces). In another instance the RISC include 3-20, 4-16, 5-15, or 6-10 LEDs.

The LEDs are preferably carried on the distal region of the LED support. The LED support preferably includes a plurality of LED contacts, each extending from a LED along an external face of the LED support to the proximal region of the LED support.

In another instance, the LEDs each include a LED emitter having an emitter face, where each emitter face is parallel to the longitudinal axis. That is, the LEDs emit radially about the LED support. Preferably, each LED includes a LED lens carried on the emitter face. That is, the emitter face is covered by a lens element, the LED lens can be flat, convex, concave, semicylindrical, or semispherocylindrical. Preferably, the LED lens is adjacent to the internal surface of the ring lens. More preferably, the LED lens has an external surface that is matched to the internal surface of the ring lens. In one instance, the LED lens can have a semicylindrical surface with a curvature that matched the internal curvature of the ring lens. For example, the internal surface of the ring lens can have an internal radius of curvature; wherein the LED lens has a LED radius of curvature; and wherein the internal radius of curvature is equal to the LED radius of curvature. In another instance, the LED lens can have a flat or plurality of flat surfaces that match to flat or a plurality of flat internal surfaces of the ring lens. In still another instance, the LED lens can have any specific shape and the internal surface of the ring lens can be match (cut or formed) to match the LED lens external surface.

In yet another instance, each LED has a LED optical axis. Herein the LED optical axis is the primary direction of emission from the LED, the optical axis is typically perpendicular to the LED chip face. Preferably, the LEDs are positioned relative to the ring lens such that a LED optical axis bisects the reflector.

The reflector preferably reflects light emitted from the LED and redirects the light to the emissions face. Accordingly, the reflector includes an internal reflection surface (a surface against which the light reflects while within the ring lens). In one instance, the internal reflection surface has a conical angle of about 35° to about 55° (the conical angle is the angle between the reflection surface and the longitudinal axis). Further qualities of the reflector were discussed in reference to FIG. 2, above. Examples of the reflector include an internal reflection surface; wherein the internal reflection surface is mirrored (herein, this means that the reflector is treated to reflect greater than 95%, preferably greater that 99% of incident light; one means for mirroring the reflection surface is the apply a layer of silver); or wherein the reflector includes an internal reflection surface; wherein a side of the internal reflection surface distal from the internal surface carries a reflective metallic coating. Still further, the ring lens can include an external surface that is mirrored.

In a preferable example, the ring lens includes an emissions face can be planar. In other examples, the emissions face can be convex, concave, convex conical, or concave conical.

In still another example, the ring lens is constructed from surgically acceptable, and optically transparent materials. In one preferably instance, the ring lens is a unitary piece of fused silica or fused quartz. In another instance, the ring lens is a transparent material, e.g. fused quartz, fused silica, sapphire, a polymer, or crown glass. In still another instance, the ring lens is a plurality of hermetically sealed transparent pieces composed of fused quartz, fused silica, sapphire, a polymer, and/or crown glass.

The RISC can further includes an electronic imaging sensor (camera) that includes an imaging array and imaging sensor electrical contacts; an array contact post including a proximal region, a distal region, an external face extending from the proximal region to the distal region, and a longitudinal axis extending from the proximal region to the distal region that is parallel to and coincident with the LED support longitudinal axis, with the imaging sensor electrical contacts adjacent to the array contact post distal region; and a plurality of array contacts in electronic communication with the imaging sensor electrical contracts and extending therefrom to the contact post proximal region. In one instance, the array contact post and the array contacts can pass through the LED support. In another instance, the electronic imaging sensor is carried upon the ring lens. In yet another instance, the electronic imaging sensor is recessed into the ring lens, wherein in one example, the imaging array is coplanar with the emissions face.

Yet another embodiment is a RISC that includes a ring lens having an emission surface, a reflector, and external surface, a lumen defined by an internal surface which extends longitudinally from the emissions face to the reflector, and an electric wire conduit port passing through the emissions face and adapted to carry an electronic imaging sensor and imaging sensor electrical contacts; and a plurality of light emitting diodes (LEDs) carried within the lumen, adjacent to the internal surface of the ring lens, and adapted to radially emit light. The RISC can further include an electronic imaging sensor adjacent to the emission surface; the electronic imaging sensor having an imaging array and imaging sensor electrical contacts. In one instance, the electronic imaging sensor is recessed into the ring lens. In another instance, the imaging array is coplanar with the emissions surface. In yet another instance, the RISC includes an array contact post in electrical contact with the imaging sensor electrical contacts, the array contact post extending through the electric wire conduit port and extending longitudinally through the ring lens. In another instance, the imaging array and imaging sensor electrical contacts are disposed about opposing surfaces of the electronic imaging sensor. In still another instance, the electronic imaging sensor is affixed to the ring lens and a plurality of imaging sensor electrical contacts in electrical contact with the electronic imaging sensor pass through the electric wire conduit port and through the ring lens.

The RISC can further include a LED support including a proximal region, a distal region, a plurality of external faces extending from the proximal region to the distal region, and a longitudinal axis extending from the proximal region to the distal region; wherein the plurality of LEDs are carried radially upon the external faces of the LED support. The RISC with the LED support can further include an array contact post adapted to carry an electronic imaging sensor, the array contact post extending through the electric wire conduit port and extending longitudinally through the LED support.

In another example, the RISC can include a ring lens which includes a working channel port passing through the emissions face, where the working channel port adapted to carry an instrument and/or fluid.

In yet another example, the RISC includes greater than 4, 5, 6, 7, 8, 9, 10, 11, 12, 13, 14, or 15 LEDs. In one instance, the RISC can include 4 to 20 LEDs, 4 to 18 LEDs, 4 to 16 LEDs, 4 to 14 LEDs, 4 to 12 LEDs, or 4 to 10 LEDs. The LEDs can be the same or selected from different emission wavelengths.

Each LED, preferably, includes a LED lens carried on an emitter face; wherein the LED lens is adjacent to the internal surface of the ring lens. In one instance, the LED lens has an external surface that is matched to the internal surface of the ring lens.

The ring lens reflector includes a reflection surface; preferably, where the reflection surface and/or the external surface are mirrored. In another instance, the ring lens includes a plurality of reflectors positioned longitudinally about the ring lens. In still another instance, the ring lens includes a plurality of reflectors positioned radially about the ring lens. In yet another instance, the ring lens includes a plurality of reflectors positioned radially and longitudinally about the ring lens. In yet another example, the ring lens is a unitary piece of fused silica or quartz.

Yet another embodiment is a ring illuminated surgical scope that includes an endoscopic cannula affixed to an endoscopic tip; and a plurality of guidewires adapted to affect the orientation of the endoscopic tip. The endoscopic tip, preferably, includes a ring illuminated surgical camera; the ring illuminated surgical camera includes a ring lens that includes an emission surface, a reflector, and external surface, a lumen defined by an internal surface which extends longitudinally from the emissions face to the reflector, and an electric wire conduit port passing through the emissions face and adapted to carry an electronic imaging sensor and imaging sensor electrical contacts; a plurality of light emitting diodes (LEDs) carried within the lumen, adjacent to the internal surface of the ring lens, and adapted to radially emit light; an electronic imaging sensor adjacent to the emission surface, the electronic imaging sensor having an imaging array and imaging sensor electrical contacts; and a plurality of imaging sensor electrical contacts in electrical contact with the electronic imaging sensor passing through the electric wire conduit port and through the ring lens. The endoscopic tip can further include at least one working channel adapted to provide instrument access and/or fluid flow to a surgical site, preferably, where the working channel passes through the emissions face.

Figure 9:
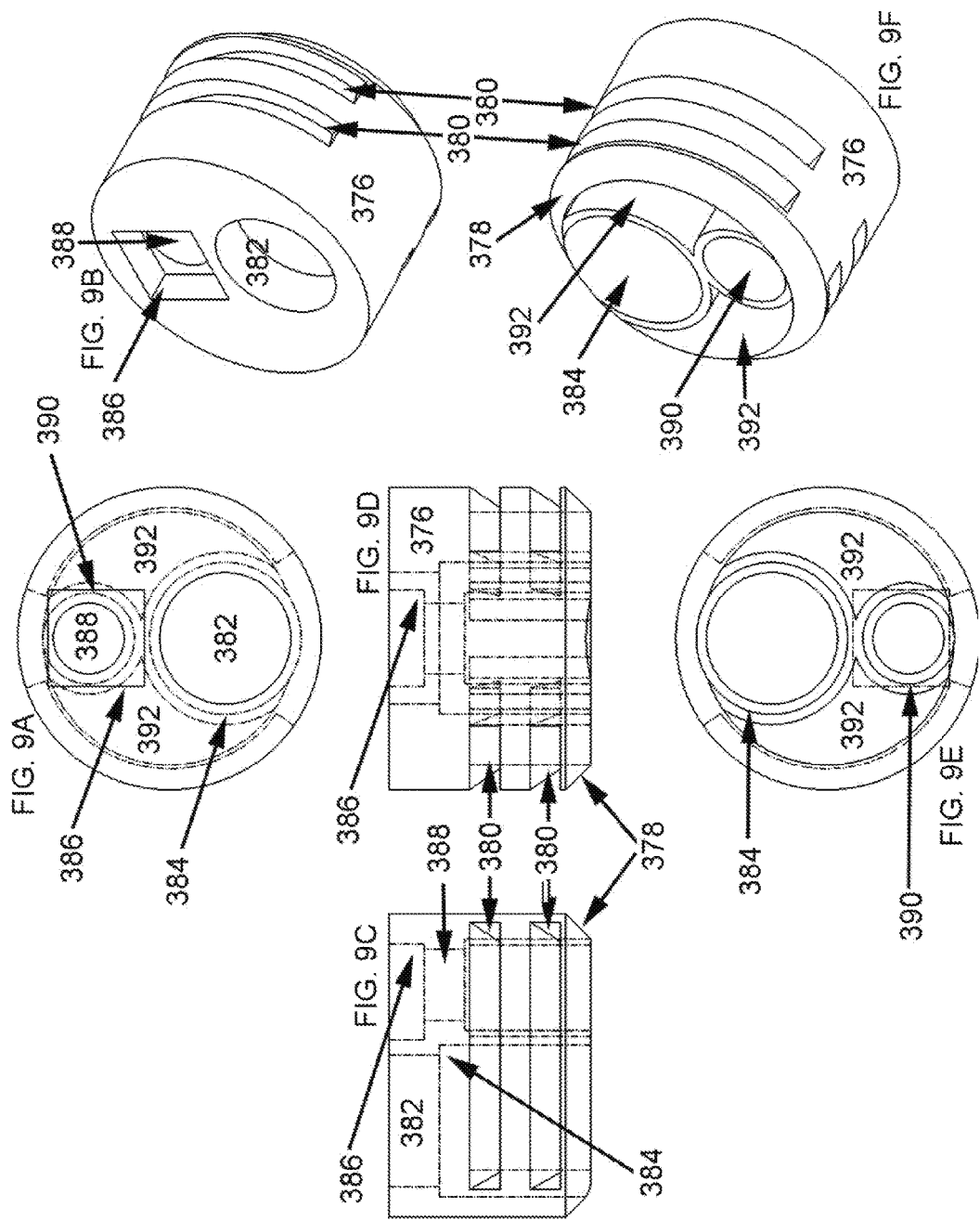
FIG. 9 shows a plurality of views of a working-channel ring lens useful in a ring illuminated surgical camera, where

Additional gains in performance within a compact geometry are available through further embodiments. FIG. 9 depicts a one contiguous piece, transparent polymer ring lens 376 that serves more functions than the prior embodiments described. The essentially cylindrical lens and housing element 376 has a chamfered 378 or stepped proximal diameter for mating to catheter tubing, equipped with TIR or reflective material coated, and partially circumferential, light reflectors 380 in the outer diameter of the cylinder, a working channel port 382 that is counterbored 384 to receive a working channel liner (not shown) and an image sensor chip (not shown) recess 386 with an electric wire conduit port 388 that is counterbored 390 for conduit attachment (not shown). The proximal side of the one-piece housing and lens 376 is hollowed out to provide space for staking LEDs (not shown) facing radially outward or at skew angles within the structural voids 392. Deflection control wires would terminate within the metal ring (not shown) that mates to the chamfer 378 or stepped OD. Furthermore and as shown in FIG. 9, the ring lens can include a plurality of reflectors 380. FIG. 9 depicts reflectors positioned radially about the ring lens (i.e., a plurality of reflectors in the same radial plane) and positioned longitudinally about the ring lens (i.e., repeating at a spacing along the longitudinal axis). In the instance shown in FIG. 9, the ring lens can include four reflectors positioned both radially and longitudinally about the ring lens.

Figure 10:
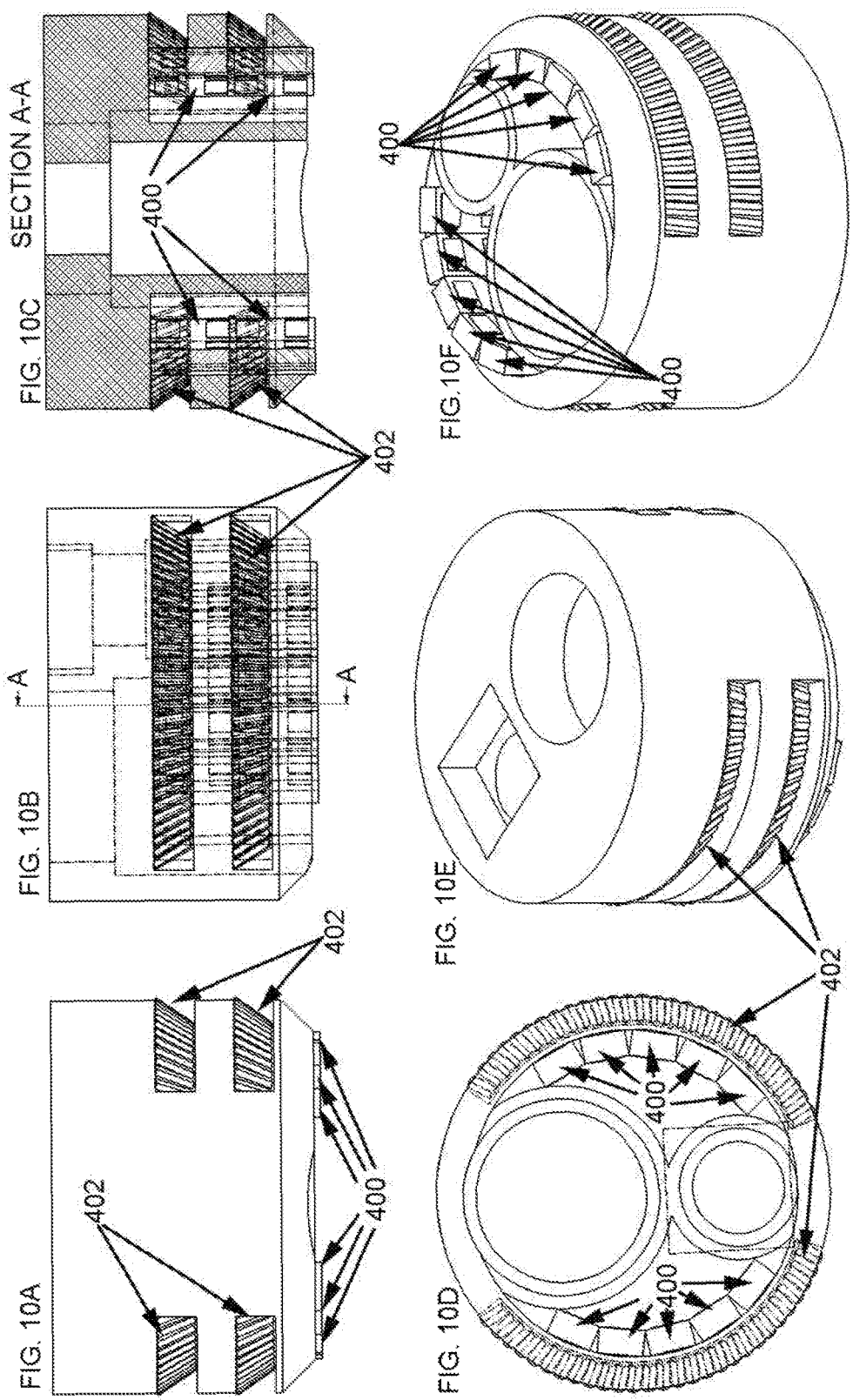
FIG. 10 shows a plurality of views of a working-channel ring lens useful in a ring illuminated surgical camera, where

LEDs 400 have been added to another embodiment based upon the concepts in FIG. 9, as depicted in FIG. 10, where the one-piece lens housing's reflective surfaces (380 in FIG. 9) have been equipped with light dispersing elements 402. Twenty LEDs 400 in all are stacked within the proximal voids (392 in FIG. 9), with the emitters (not visible) pointed radially outward at the reflectors 380. Uniformity of illumination may be further controlled by adding off radial mounting within the available space 392 and/or divergence altering lenses on the LEDs.

Still further, the RISC can include one or more camera lenses set before the electronic imaging sensor. In one instance, a camera lens can be coplaner with the emission surface of the ring lens. In another instance, a camera lens can be carried above (distal to) the ring lens. In still another instance, the camera lens can be integral to the ring lens; that is, in one example with reference to FIG. 4B, the ring lens can include a window 314 that is adapted to focus light reaching the electronic imaging sensor. Notably, the window 314 can be integral to the ring lens 312 (e.g., one piece of fused silica, quartz, or plastic). In still another instance, the RISC includes a plurality of camera lenses set before the electronic imaging sensor and adapted to focus light onto the sensor. In yet another embodiment, the relative positions of one or more lens can be adjusted (e.g., moved along the longitudinal axis) to affect the focus of light on the sensor.

Figure 11:
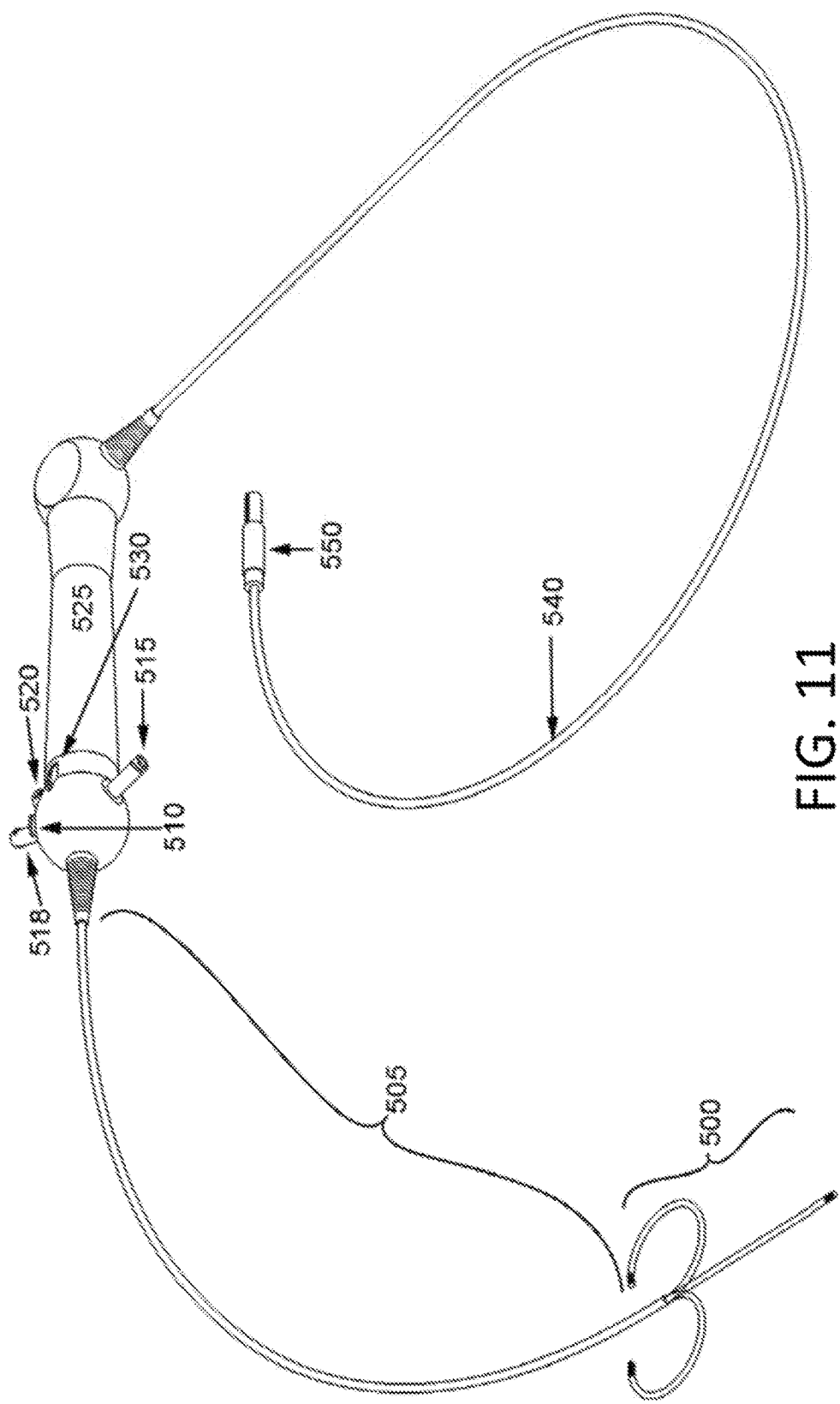
FIG. 11 is a depiction of an endoscopic tool showing the deflection of the distal end 500 and the control and connections on the proximal end.

Preferably, the above embodiments of the RISC are included in an endoscopic device, for example a ureteroscope or duodenoscope. In reference to FIG. 11, an endoscope is shown to illustrate the common parts of the device Materials of differing durometer that are compatible with ethylene oxide gas or other sterilization methods are selected to provide the greatest flexibility at the distal several centimeters of the device 500 where deflection occurs via movement of steering wires (333 in FIG. 6) under control of a wheel 530 or lever or button on the scope handle 525, as known in the art. The working channel port 520 is typically housed upon a Luer type Y-fitting to permit tool access via one port and an irrigation fluid connection 518 via the other port of the Y-fitting. This Y-fitting is unnecessary given the auxiliary lumen in the present invention—that is, the working channel may remain dry—but the capacity to utilize the working channel for fluid flow may be retained as an option for surgical cases where higher flows are desirable. An auxiliary port(s) 515 may be provided for accessing the auxiliary lumen, in unison or individually, for fluid inflow (irrigation) or as a drain.

One or more pushbuttons, switches or other selectors 510 may be provided to select among alternative flow modes, e.g. irrigant inflow via the working channel 518 and auxiliary lumen 515 with standard drainage about the scope body 505, inflow via the working channel with drainage via the auxiliary lumen port 515, and alternative lighting modes, e.g. white only, white plus blue, white plus UV, all on. A dimmer may also be provided. Alternatively, lighting control may be provided upon the control or display console (not shown), connection to which is provided by the electronics communication cable 540 and multi-contact connector 550.

FIGS. 12-14 show a plurality of examples of endoscopic terminations (carried on the distal end 500 of the endoscope) having working channels or lumen angled relative to the longitudinal axis of the endoscopic termination and/or the endoscopic tip. Herein the term "working channel(s)" includes the channel, channels, or lumen that are operationally connected to the endoscopic termination and can be used during a surgical procedure. Unless specifically distinguished by function, the term "working channel" herein includes an instrument channel (e.g., a channel that carries a forceps or other tool), an irrigation channel, a biopsy channel, a suction channel, and/or an air channel. Furthermore, the term "working channel" includes auxiliary lumen or auxiliary channel(s), where the auxiliary lumen is typically not an instrument channel. Herewith, when the endoscopic termination includes a plurality of working channels, these channels can be selected from an instrument channel, an irrigation channel, a biopsy channel, a suction channel, an air channel, and combinations thereof. Moreover, each "working channel" can provide one or more functions, for example a working channel can be an instrument channel and an irrigation channel.

In one embodiment, the endoscopic tip, specifically the hard portion carried on the distal end of the endoscope, carries the RISC, one or more angled working channels or lumen, and is affixed to a cannula or tube (not shown). FIG. 12 depicts one example, where FIG. 12A shows an end on view, FIG. 12B shows a side view, and FIG. 12C shows a transparent perspective view. Therein, the endoscopic tip 610 can include a chamfer 609 for affixing a cannula or tube thereto, a radial face 608 or body that is optionally exposed past the distal end of the cannula or tube, and at least one distal face 611 that can include a perpendicular distal face (relative the longitudinal axis) and a chamfered or filleted face 614 that can include terminations for working channels. In one instance, the distal face 611 includes a perpendicular distal face 613 and a chamfered or filleted face 614. Herein, the chamfered or filleted face can be planar (flat) or can have a curvature. In one instance, the chamfered or filleted face 614 have an angle relative to the perpendicular distal face of greater than 90°, preferably greater than about 100°, 110°, 120°, 130°, or 140°. In one instance, this angle is in a range of about 100° to about 150°, about 105° to about 135°, or about 105° to about 125°. When the chamfered or filleted face 614 has a curvature, the angle is relative to the tangent of the curvature. In one instance, the chamfered face is perpendicular to the working channel 626 longitudinal axis; in another instance, the chamfered face is angled relative to the working channel longitudinal axis. In still another instance, the distal end of the working channel is adjacent to both the perpendicular face and the chamfered face.

The endoscopic tip 610 includes a RISC bore 635 within which can be carried ring lens 625 and an electronic imaging sensor 627. Preferably, the endoscopic tip 610 further includes one or more working channels or lumen. Herein, working channel(s) or lumen refer to either or both the channel through which endoscopic tools can pass (commonly known as the working channel) and/or the irrigation channel. In the FIGS. 12 and 13, the endoscopic tips are shown with three working channels distinguished by internal diameter, whereas in FIG. 14 the endoscopic tip is shown with one working channel. Preferably, the endoscopic tip has at least one working channel adapted for tools and/or irrigation. Further examples include one working channel, or a plurality of working channels, including two working channels, three working channels, four working channels, five working channels, or 6+ working channels.

FIG. 12 includes a first working channel 620, preferably adapted for passing an endoscopic tool therethrough, and a plurality of second working channels 622, e.g., adapted for irrigation of a surgical site. The first working channel can be affixed to a first cannula or tube 623 and the second working channel can be affixed to a second cannula or tube 626. As shown in FIG. 12B, the first and the second cannula (623 and 626) can have longitudinal axes that are non-parallel to the longitudinal axis of the endoscopic tip 610. That is, the working cannula, like the working channel, can be angled relative to the longitudinal axis of the endoscopic tip. In one instance, the angle between the longitudinal axis of the endoscopic tip and the longitudinal axis of the working channel and/or the working cannula is about 1°, 2°, 3°, 4°, 5°, 6°, 7°, 8°, 9°, 10°, 11°, 12°, 13°, 14°, 15°, 16°, 17°, 18°, 19°, or 20°. In another instance, the angle is between about 1° and about 25°, about 2° and about 20°, or about 5° and about 15°. When the endoscopic tip includes a plurality of working channels, the working channel longitudinal axes can be parallel, in another instance the working channel longitudinal axes are non-parallel (e.g., a first channel has an angle that is at least 1° different than a second angle).

FIG. 12C further shows details internal to the endoscopic tip 610. In one instance, the endoscopic tip can include working channel chamfers adapted to carry the cannula affixed to the respective working channels. In one instance, the endoscopic tip can include a first working channel 620 that includes a first working channel chamfer 621 adapted to carry the first cannula 623. The endoscopic tip can further include at least one second working channel 622 that includes a second working channel chamfer 624 adapted to carry the second cannula 626. The endoscopic tip can still further include one or more guide wire attachments 632 adapted to carry the distal end of endoscopic guide wires (not shown). Still further the endoscopic tip can include a RISC lumen 630 that is adapted to carry connections to the LEDs and electronic imaging sensor.

The angled working channel lumen 700 and auxiliary lumen 702, detailed in FIG. 13, further aids miniaturization of the scope tip 800 diameter 705 while offering far superior irrigant flows than the prior art. Most ureteroscopes utilize the working channel 700 for both tool access and irrigant flow. In laser URS, for example, the surgical site is filled with saline (or ringers) and flow is maintained with the tool (e.g. optical fiber, basket, etc.) in place. Drainage occurs about the outer diameter of the scope, in a space between the ureter/urethra and the scope surface, or more commonly, between a "ureteral access sheath" and the scope surface, with maximum flow restricted by the occlusion of the working channel lumen by the tool (e.g. laser fiber, stone basket).

Where flows are inadequate, the surgical site must be drained and refilled as visualization becomes problematic due to fragments of urinary calculus floating in the surgical field. Drainage may be hampered by larger particles of calculus, sometimes requiring the scope to be removed and replaced.

Larger tools occlude flows more than smaller tools. Using the Boston Scientific LithoVue™ disposable ureteroscope as an example, the working channel is 1.08 mm in diameter, or 3.6 Fr. where a typical "365 micron" optical fiber for laser URS is 0.6 mm (2 Fr.), blocking roughly $\frac{1}{3}^{rd}$ of the lumen volume and producing an effective lumen diameter for flow of 0.9 mm (3 Fr.). The smallest generally available fiber for laser URS ("200 micron") is less occlusive at 0.4 mm diameter and only moderately affects the flow of irrigation where the largest fiber ("550 micron") that will fit in the scope effectively halves flow.

Larger working channels offer a clear advantage in permitting use of larger diameter tools, when desirable or necessary, and in providing superior irrigation flow. In competition with these advantages is the overall diameter of the scope itself because larger diameter scopes (a) are more limited in ability to access all body cavities (b) are typically less flexible and (c) block more drainage of irrigation about the scope. Minimization of scope diameter is limited by the short, rigid scope tip dimensional requirements where the tip must provide, at a minimum, lighting, visualization, tool access and irrigation (the latter two typically being combined).

Clustering of component lumen is limited by the necessity to maintain isolation of the camera/sensor/lighting electronics from sterile irrigant flow or intrusion. It is further preferable to shield the camera and its power and image conductors from electromagnetic interference where electrocautery tools are used. Shielding takes space so it is not commonly found in modern ureteroscopes, resulting in recurrent loss of image during electrosurgical procedures.

A further consideration is accidental perforation of the working channel by tools progressing two and from the surgical site via the lumen in question. Most laser fibers present sharp edges that may score or puncture the working channel, particularly when passed through the lumen while under deflection: it is therefore insufficient to protect the electronics only from outside intrusion of liquids. The endoscopic tip 800 (e.g., a rigid ureteroscope tip body) depicted in FIG. 13 (without electronics or fluidic conduits attached) provides for secure, air-tight seals for four separate lumen within counterbored ports in the proximal face 804 and FIG. 9C of the rigid scope tip body: one working channel at counterbore 805, two auxiliary/irrigation channels at counterbores 810, and one electronics channel at counterbore 815. All four bores meant for mating to tubes are tilted at a low angle off the longitudinal axis of the rigid scope tip body 800. (Mating fluidic communications lumen, tool access lumen and electronics carrying lumen may be accomplished by any means known in the art; adhesively fixing tubes within counterbored lumen is merely a simple example.)

Canting the lumen in the endoscopic tip 800 is effective because the camera sensor counterbore 812 is larger at the distal face 806 FIG. 13A of the tip than the electronics carrying lumen 704 counterbore 815 need be at the proximal face 804 of the tip; more area is available on the proximal face FIG. 9C (804) than the distal face FIG. 13A (806).

Two bores in proximal face 804 of the rigid body are not tilted with respect to the longitudinal axis: the threaded steering wire anchor points 808. Anchoring steering wires may be accomplished by threads, as depicted, or numerous other means know in the art, e.g. looping, crimping, adhesively fixing. Further, the camera sensor counterbore 812 is not tilted.

FIG. 14 depicts the preferred embodiment for a low cost, high performance, single use ureteroscope. FIG. 14C is the distal face 900 of the scope tip 990 within which is flush-mounted the hexagonal ring lens 905 housing the camera sensor 910 with contacts 911 oriented proximally, protective window 915 and a plurality of LED 920 light sources, electrical contacts 921 oriented generally toward the longitudinal axis, as in prior examples. In the embodiment, the sole penetration through the scope, to the scope tip, is the working channel lumen 925 that may be aligned off parallel 903 to the longitudinal axis slightly to facilitate retention of adequate wall thicknesses for counterbores 916 and 924, wherein the electronics communications tube 918 and working channel liner 922 are secured, respectively.

The hexagonal ring lens 905 arrangement presents a narrower dimension 930 than the equivalent square lens yet continues to offer relatively equivalent lighting from each of the camera sensor's 910 four sides from six LEDs 920 as in the cross-section at FIG. 14D. The smaller aspect of the hexagon permits an increase in the diameter of the working channel relative to prior art, and the associated benefits therein realized.

Two threaded bores 935 are produced at the proximal face 940 of the rigid scope tip 990 for securing the deflection control wires 950. The working channel tube 922 and electronics communications tube 918, the latter lumen 995 containing the video data cable and power conductors, not shown, are housed within a polymer sheathed 943 braid or strip wound material 938 or other protective, yet flexible tubing material, secured on the scope tip 990 at a reduced diameter 945 portion of the rigid tip.

While the descriptions herein have concentrated upon ureteroscopic applications, the concepts taught apply to other endoscope designs. Notably, the descriptions and designs provided herein are free of optical fiber. Preferably, the devices are free of optical fiber, this, in part, permits a reduction in the diameter of the device. While the compositions and methods of this invention have been described in terms of preferred embodiments, it will be apparent to those of skill in the art that variations may be applied to the compositions and/or methods in the steps or in the sequence of steps of the method described herein without departing from the concept, spirit and scope of the invention. More specifically, it will be apparent that certain agents that are both chemically and physically related may be substituted for the agents described herein while the same or similar results would be achieved. All such similar substitutes and modifications apparent to those skilled in the art are deemed to be within the spirit, scope and concept of the invention as defined by the appended claims.

What is claimed:

1. A diagnostic and/or surgical device comprising:
   an endoscopic tip having
      a distal face which has a RISC bore and a working channel opening,
      an endoscopic tip longitudinal axis running from the distal face to a proximal end,
      a working channel running from the working channel opening on the distal face to the proximal end and having a working channel longitudinal axis that is non-parallel to the endoscopic tip longitudinal axis, and
      a RISC lumen running from the RISC bore on the distal face to the proximal end, and carrying a ring illuminated surgical camera which includes
         a ring lens having an emission surface,
         a plurality of light emitting diodes (LEDs) adjacent to an internal surface of the ring lens, and adapted to radially emit light, and
         an electronic imaging sensor adjacent to the emission surface.

2. The diagnostic and/or surgical device of claim 1 further comprising a working channel angle of between about 1° and about 25° between the working channel longitudinal axis and the endoscopic tip longitudinal axis.

3. The diagnostic and/or surgical device of claim 2 comprising a plurality of working channels, each working channel having a working channel longitudinal axis.

4. The diagnostic and/or surgical device of claim 3, wherein the working channel longitudinal axes are parallel to each other.

5. The diagnostic and/or surgical device of claim 1, wherein the distal face includes
   a perpendicular distal face that is perpendicular to the endoscopic tip longitudinal axis and
   a chamfered face.

6. The diagnostic and/or surgical device of claim 5, wherein the chamfered face is perpendicular to the working channel longitudinal axis.

7. The diagnostic and/or surgical device of claim 5, wherein the chamfered face is angled relative to the working channel longitudinal axis.

8. The diagnostic and/or surgical device of claim 5, wherein the working channel opening is adjacent to both the perpendicular distal face and the chamfered face.

9. The diagnostic and/or surgical device of claim 1, wherein the ring illuminated surgical camera includes
   the ring lens having the emission surface, and further including
      a reflector,
      an external surface,
      a lumen defined by an internal surface which extends longitudinally from the emission surface to the reflector, and
      an electric wire conduit port passing through the emission surface and adapted to carry an electronic imaging sensor and imaging sensor electrical contacts;
      wherein the plurality of light emitting diodes (LEDs) are carried within the lumen; and
      wherein the electronic imaging sensor has an imaging array and imaging sensor electrical contacts.

10. The diagnostic and/or surgical device of claim 1 further comprising an endoscopic cannula affixed to the endoscopic tip.

11. The diagnostic and/or surgical device of claim 1, wherein the diagnostic and/or surgical device is free of optical fiber.

12. A device comprising:
   a ring illuminated surgical camera that includes
      a ring lens that includes
         an emission surface,
         a reflector,
         an external surface,
         a lumen defined by an internal surface which extends longitudinally from the emission surface to the reflector, and
         an electric wire conduit port passing through the emission surface;
      a plurality of light emitting diodes (LEDs) carried within the lumen, adjacent to the internal surface of the ring lens, and adapted to radially emit light;
      an electronic imaging sensor adjacent to the emission surface, the electronic imaging sensor having an imaging array and a plurality of imaging sensor electrical contacts, the electronic imaging sensor being carried by the electric wire conduit port; and
      the plurality of imaging sensor electrical contacts being in electrical contact with the electronic imaging sensor passing through the electric wire conduit port and through the ring lens the plurality of imaging sensor electrical contacts being carried by the electric wire conduit port;
   the ring illuminated surgical camera carried in a recess of an endoscopic tip;
   the endoscopic tip affixed to a endoscopic cannula;

the endoscopic tip including at least one working channel having a working channel longitudinal axis that is non-parallel to an endoscopic tip longitudinal axis;

the at least one working channel affixed to a working channel cannula which is carried within the endoscopic cannula; and a plurality of guidewires affixed to the endoscopic tip, carried within the endoscopic cannula, and adapted to affect the orientation of the endoscopic tip.

13. The device of claim 12, wherein the endoscopic tip includes a distal end, wherein the distal end includes a first surface which is perpendicular to the endoscopic tip longitudinal axis, and wherein the electronic imaging sensor of the ring illuminated surgical camera is parallel with the first surface of the distal end of the endoscopic tip.

14. The device of claim 12, wherein the endoscopic tip includes a distal end, wherein the distal end includes a first surface perpendicular to the endoscopic tip longitudinal axis and a second surface non-perpendicular to the endoscopic tip longitudinal axis, and wherein the ring illuminated surgical camera is carried in a recess on the first surface.

15. The device of claim 14, wherein at least one working channel includes an opening in the second surface.

* * * * *